United States Patent
Gianturco

(10) Patent No.: US 7,611,495 B1
(45) Date of Patent: Nov. 3, 2009

(54) DEVICE FOR MANUALLY CONTROLLING DELIVERY RATE OF A HYPODERMIC SYRINGE AND SYRINGE HAVING SAME

(76) Inventor: Michael C. Gianturco, 940 Park Ave., New York, NY (US) 10028

(*) Notice: Subject to any disclaimer, the term of this patent is extended or adjusted under 35 U.S.C. 154(b) by 0 days.

(21) Appl. No.: 11/245,827

(22) Filed: Oct. 7, 2005

(51) Int. Cl.
*A61M 5/00* (2006.01)
*A61M 5/315* (2006.01)

(52) U.S. Cl. .................. 604/207; 604/208; 604/227

(58) Field of Classification Search ......... 604/207–211, 604/220, 224, 227–228, 187, 218, 219, 223, 604/229, 233; 73/864.14, 864.16, 864.18
See application file for complete search history.

(56) References Cited

U.S. PATENT DOCUMENTS

| 2,943,624 | A | * | 7/1960 | Alquist | 604/210 |
|---|---|---|---|---|---|
| 4,018,223 | A | * | 4/1977 | Ethington | 604/207 |
| 4,444,335 | A | * | 4/1984 | Wood et al. | 222/43 |
| 4,465,478 | A | * | 8/1984 | Sabelman et al. | 604/224 |
| 4,687,472 | A | * | 8/1987 | Gross | 604/223 |
| 5,115,816 | A | | 5/1992 | Lee | |
| 5,135,511 | A | * | 8/1992 | Houghton et al. | 604/220 |
| 5,250,030 | A | | 10/1993 | Corsich | |
| 5,346,475 | A | | 9/1994 | Gregorio | |
| 5,531,691 | A | | 7/1996 | Shonfeld et al. | |
| 5,562,623 | A | | 10/1996 | Shonfeld et al. | |
| 5,582,595 | A | * | 12/1996 | Haber et al. | 604/187 |
| 6,231,550 | B1 | * | 5/2001 | Laughlin | 604/187 |
| 6,283,941 | B1 | | 9/2001 | Schoenfeld et al. | |
| 6,533,756 | B2 | | 3/2003 | Schoenfeld et al. | |
| 6,719,735 | B1 | | 4/2004 | Gammon | |
| 2003/0004467 | A1 | | 1/2003 | Musick et al. | |
| 2005/0215958 | A1 | * | 9/2005 | Hawthorne | 604/227 |

FOREIGN PATENT DOCUMENTS

| DE | 10235468 | 8/2002 |
|---|---|---|
| GB | 2140302 | 11/1984 |
| JP | 2000-296178 | 10/2000 |

* cited by examiner

*Primary Examiner*—Kevin C Sirmons
*Assistant Examiner*—Catherine N Witczak
(74) *Attorney, Agent, or Firm*—Barry E. Negrin, Esq.; Pryor Cashman LLP

(57) ABSTRACT

An injection retarder for mechanically/manually reducing the rate of delivery of a hand-held hypodermic syringe and a syringe having same are provided. The injection retarder and syringe include means for selectively slowing a rate of progress of the plunger into the barrel. For example, a thumb tip rest is provided against which the thumb may be braced, thereby providing additional mechanical advantage and much finer manual control of the rate of injection. Alternatively, a set of teeth and an opposing mating tooth or pawl are provided which increase friction and slow the progress of the plunger.

19 Claims, 19 Drawing Sheets

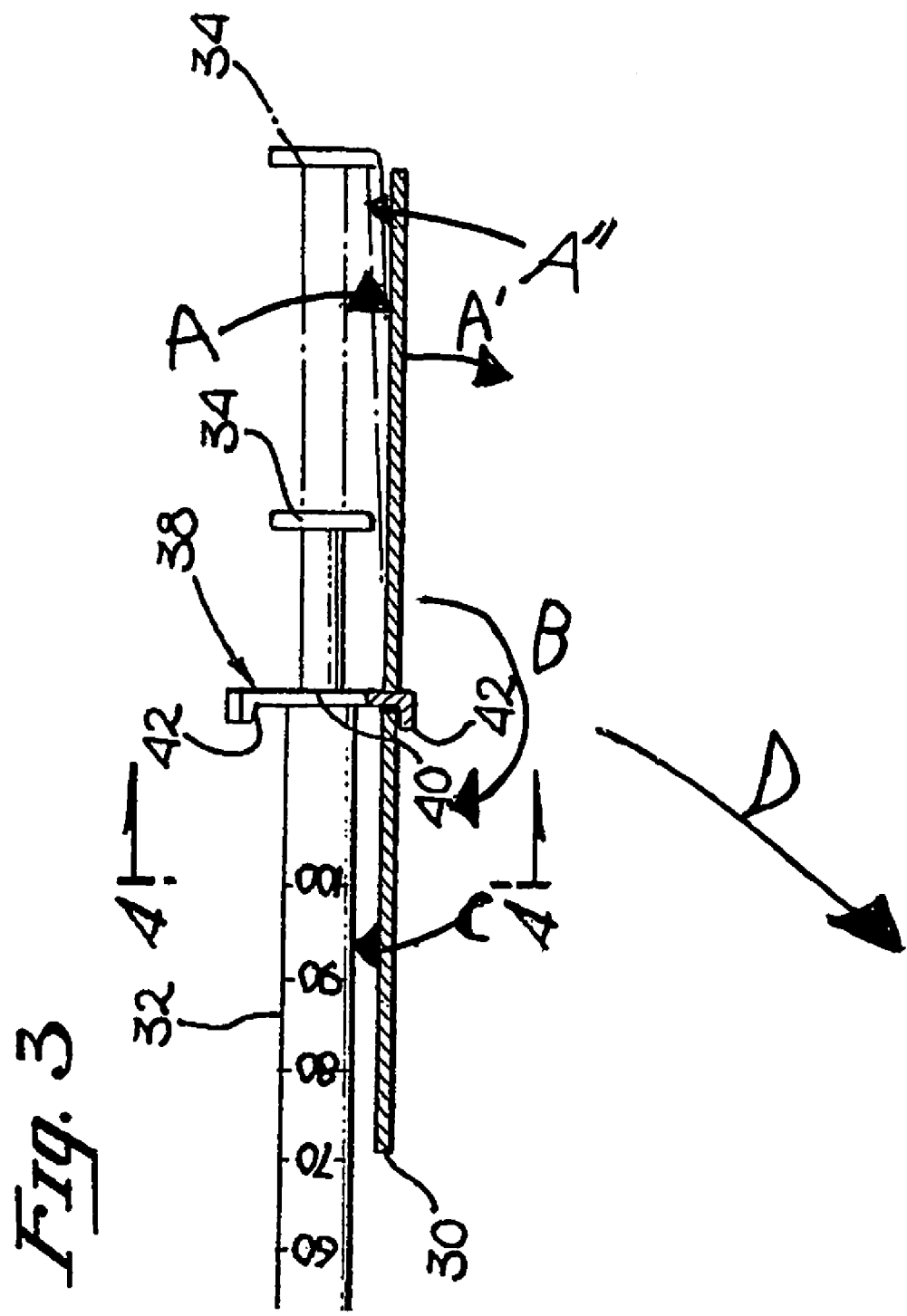

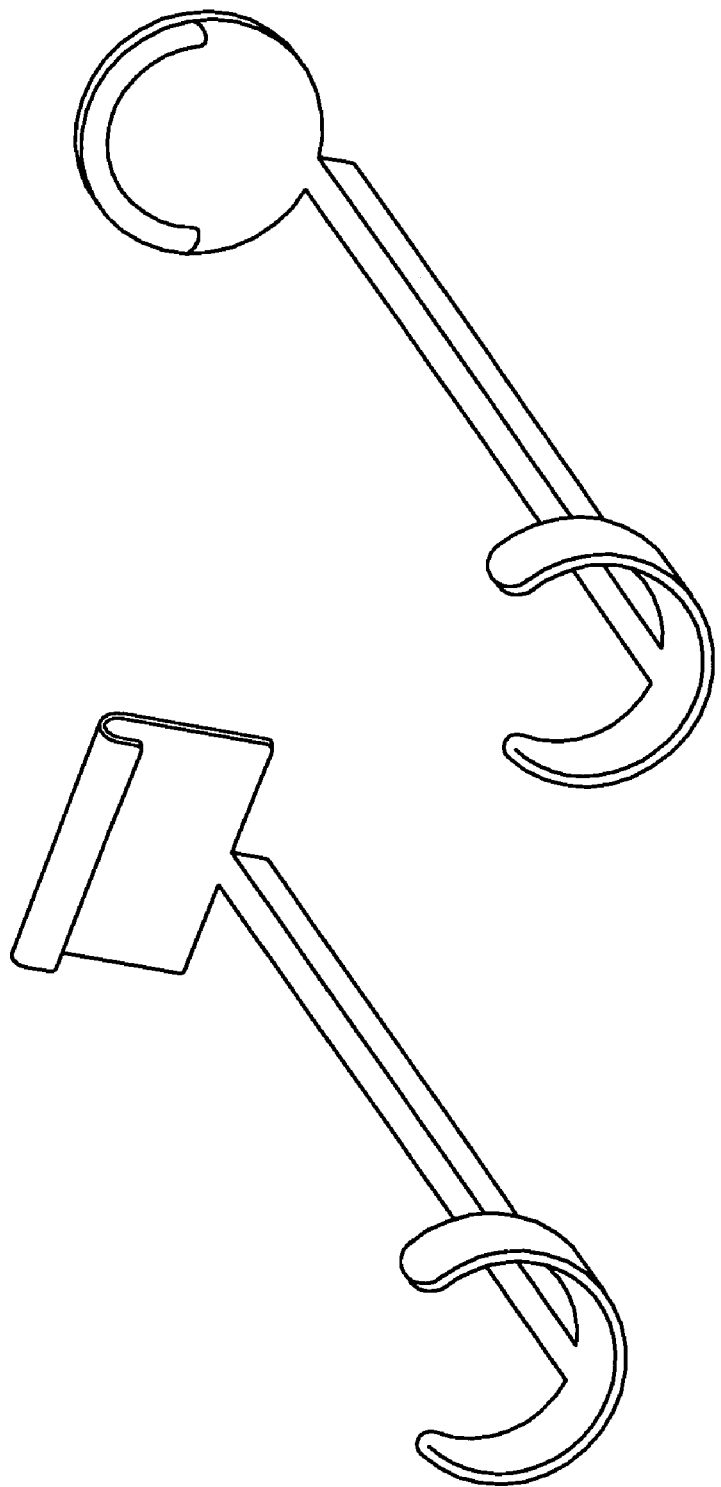

DEVICE FOR MANUALLY CONTROLLING DELIVERY RATE OF A HYPODERMIC SYRINGE AND SYRINGE HAVING SAME

BACKGROUND OF THE INVENTION

1. Field of the Invention

The invention is related to hypodermic syringes. More specifically, the invention is related to devices for controlling or slowing the rate at which a hypodermic syringe dispenses its contents when manually operated.

2. Description of the Related Art

Most syringes are made of plastic. Plastic syringes are mass-produced and disposable. A typical syringe includes a plastic barrel and a plastic plunger having an elastomeric seal, or stopper, at its distal end inside the barrel. The plunger is reciprocatable inside the barrel. The barrel typically has a pair of flanges at its proximal end under which the user places his index and middle fingers. The plunger typically has a head, or thumbpad, at its proximal end upon which the user places his thumb.

To dispense medicine contained in the syringe barrel, the user increases the pressure applied by his or her thumb to the plunger head, while applying opposing (supporting) pressure with two fingers on the flanges of the barrel. Owing to the pressure of the thumb on the head of the plunger, the plunger advances into the barrel and forces the medication out via the needle. Syringe lubricant is included by the syringe manufacturer to allow the stopper to slide more easily within the barrel. Polydimethyl siloxane fluid is a typical syringe lubricant.

The benefits of disposable plastic syringes include low cost and increased patient safety. However, along with the benefits of plastic syringes has come an inherent problem: It is commonly and aptly described as "stick-slip" behavior. The "stick-slip" effect makes it quite difficult to inject medication slowly.

What are the benefits of slow injection? The first is comfort. Regardless of medication, a slow injection is typically less painful than a rapid injection. For some medications (e.g. heparin) sudden injection can actually be quite uncomfortable for the patient. The second benefit of slow injection is, in some cases, better end results, probably owing to better assimilation of slowly injected medication by cells in the injected tissue. Increased effectiveness associated with slow injection rates has been demonstrated, for examples, in certain anaesthetic injections and in some inoculation procedures. In such cases the advantage to the individual patient of a slowly delivered, finely incremented injection include either 1) a reduced dose to produce the same benefit or 2) a quicker or more vigorous benefit produced by the same dose.

Slow injection offers economies of scale. In applications where it can be shown to produce an enhanced end result a reduced dosage might be prescribed. For an individual patient using medicine to treat a chronic condition, injecting daily for example, a slight daily reduction in dosage could add up to a significant reduction in the total amount of medicine injected over a period of years. Similarly, in a mass inoculation program conducted with limited supplies of a vaccine, there could be a social gain based simply on the conservation of vaccine. At present, the possibilities of such economies of scale have not been fully explored since costly and specialized motor-driven syringes must be used for slow metering of injected volumes.

Why do plastic syringes make it difficult to perform slow injections? First they stick and then, suddenly, they slip. To start an injection, significant thumb pressure, called the "break out" force, must be applied to the syringe plunger to overcome static friction and put the plunger in motion. However, in the instant the threshold of the "break out" force is exceeded the plunger friction decreases dramatically and without warning. As a result the syringe plunger, which is still receiving very strong pressure from the thumb, suddenly surges into the syringe barrel.

The plastic syringe plunger's transition between "stick" and "slip" is so very quick that the human being operating the syringe is usually incapable of backing off the thumb pressure in time to prevent the sudden downward surge of the plunger. The result is that fluid is dispensed from the syringe and into the tissue as a large bolus, or slug, of medication.

A slow, steadily progressing injection stroke is difficult for anyone to achieve with a plastic syringe, and it is especially difficult for non-professionals who may be required to self-inject. Stick-slip behavior is a particularly noticeable problem if only a few units are required to be manually injected slowly. For example, for a 5-unit manual injection from a 50-unit capacity U-100 type Becton Dickinson disposable insulin syringe, the entire injection of 5 units may be delivered in just two abrupt surges, owing to the stick-slip properties of the syringe. Thus, the syringe delivers to the tissues two successive boluses of medication, one right after the other—rather than a slow, incrementally metered stream.

Stick-slip behavior arises from the interaction of the elastomer used to manufacture the syringe seal, or stopper; the syringe lubricant; and the syringe cylinder. To some degree, it is characteristic of all disposable plastic syringes. Stick-slip is a velocity dependent phenomenon, and it is most troublesome in slow injections. In addition to interfering with slow dispensing of medicine from a plastic syringe, the inherent stick-slip action of a plastic syringe makes it tricky to precisely and quantitatively load the syringe, particularly if fractional volume units are desired. The piston has a tendency to "jump" past the desired increment mark or position.

Another problem arises from the wrong kind of leverage. In the example of the poorly controlled 5-unit injection noted above, the thumb, pivoting at a center located at its base joint at the wrist, quickly traverses through a tiny angular displacement of just 2-3 degrees in delivering a dose of 5 units. The thumb, like most anatomical levers, is a third class lever. It operates at a mechanical disadvantage. Muscular effort is sacrificed in a lever of this type in order to gain distance and, therefore, speed. The thumb is configured for sudden movement. A tiny angular displacement about the center (that is, the joint) located at the base of the thumb results in a large, sudden displacement of the syringe plunger by the thumbtip. The longer the thumb, the faster the thumbtip will move for a given angular displacement. From the standpoint of fine control and slow injection, this geometry is certainly not helpful. Moreover, the high breakout force required to overcome the molecular interaction between the elastomeric stopper and the plastic syringe barrel begs for an increase in mechanical advantage—not speed.

Prior efforts to ameliorate the problem include chemical modification of the crosslinking of dimethyl siloxane syringe lubricants. The idea was to diminish static friction, that is, to reduce the "stick" component of the stick-slip effect. Changing the lubricant chemistry reportedly helped, but different medications may require different lubricants for optimum results. Changes in lubricant chemistry may also be required to optimize injections at different rates. In any event, a better lubricant is only a small initial step toward a solution. Lubrication can only alleviate, to some degree, the "stick", or static friction problem. But in a manual syringe the "slip" and the surge injection it produces must also be addressed.

A low cost, widely applicable solution that is independent of injection rate, and of the specific type of medication to be injected is needed. The inventive solution needs to do two things: 1) overcome the syringe's "stick", or static friction, and then 2) limit or actively arrest the subsequent "slip" and surge.

SUMMARY OF THE INVENTION

The above and other issues are addressed by the invention, which is a device for mechanically/manually reducing the rate of delivery of a hand-held hypodermic syringe and a syringe having same. The add-on device will be referred to as an injection retarder. The invention controls and retards the rate of injection through the application of second class leverage or braking. Both effects, leverage and braking, can be achieved with the same device.

In one embodiment, the inventive injection retarder has a main body with a clip securable onto a hypodermic syringe; the main body at least partially extending above the barrel adjacent to a plunger of the syringe when secured to the syringe. The injection retarder includes means for selectively slowing a rate of progress of the plunger into the barrel.

In one embodiment, the progress slowing means includes a thumb tip rest formed at a proximal end of the main body adapted to allow a user to place a tip of a thumb thereupon during dispensing of contents of the syringe. The injection is performed by extending the thumb, rather than flexing it as in conventional practice. As the thumb is extended, it rocks downward onto the syringe plunger.

When the user applies force to the head of the plunger, with the tip of the thumb pivoting against the thumb tip rest, force is substantially applied about an axis through the upper thumb joint (as opposed to joint where the thumb attaches to the wrist with conventional syringe usage).

In effect, the invention shifts the fulcrum of the lever (that is, the thumb) from its base at the wrist to the thumbtip. This fulcrum shift alters the leverage of the thumb from third class to second class. An example of a second class lever is a garlic press. Second class leverage gives the thumb a generous mechanical advantage, so that it can very easily overcome the inherent stickiness, or static friction, of the plunger. It also produces as much as a tenfold increase in the range of motion (that is, angular displacement) of the thumb for a given injected volume, contributing to a much improved fineness of control. Finally, the thumb rest anchors the thumbtip, so that the thumb does not tend to pursue and drive the plunger after the piston starts to slip. As a result, there is no surge injection. As the thumb is gradually extended and rocked downward, the injection proceeds in a series of tiny, incremental downward budges of the plunger. For a 50 unit disposable syringe with the invention in place, each incremental advance of the plunger delivers as little as 0.3 units of medication into the injected tissue. Thus, the injection can be halted at will after any 0.3-unit pulse of medication.

The thumb tip rest is preferably a flat surface onto which one places one's thumb. The thumb tip rest may be a substantially vertical surface extending substantially parallel to a longitudinal axis of the syringe barrel. In this embodiment, the thumb tip is pressed against the vertical surface and the first joint of the thumb is rocked downward against the head of the plunger to press against the plunger to dispense medicine. The vertical surface may be provided with a significantly higher coefficient of friction than the rest of the main body so the thumb tip does not slip. In addition or in the alternative, the vertical surface may have teeth adapted to accommodate the thumb tip of a user between adjacent of the teeth. Preferably, the vertical surface is sufficiently close to the plunger so that at least the head of the plunger is laterally pressable against the vertical surface while the plunger is being pushed downward into the barrel. In such a mode of operation, the higher coefficient of friction (or the teeth, or both) creates a resistive force that retards the descent of the plunger into the barrel when the user presses the head of the plunger against the vertical surface while pushing the plunger downward into the barrel.

As another alternative, the thumb tip rest may be a substantially horizontal surface extending above the proximal end of the barrel and substantially perpendicular to a longitudinal axis of the syringe barrel. In this embodiment, the thumb tip is pressed against the horizontal surface and the first joint of the thumb is rocked downward against the head of the plunger.

In any of the embodiments, the inventive injection retarder may include a plunger stop secured to the main body and extending above the barrel and in the path of the head of the plunger. When a user presses down on the plunger head, the plunger moves into the barrel until the plunger head abuts the plunger stop. The inventive syringe brake may also include finger grip indentations formed in a side of the main body opposite the clip.

In another type of embodiment, generally, the progress slowing means is a means for increasing a dynamic frictional force exerted by the plunger against the force exerted by the user in depressing the plunger. More specifically, the progress slowing means may include a plurality of teeth formed on one of the plunger or barrel and the main body and a mating tooth formed on the other of the plunger or barrel and the main body. The mating tooth is abuttable against the plurality of teeth when the plunger is pressed into contact with the main body. Pressing the mating tooth against the plurality of teeth creates a resistive force that retards the descent of the plunger into the barrel when the plunger is also pushed into the barrel. In one version, the main body is made resilient and biases the mating tooth against the plurality of teeth on the barrel when the clip is secured to the head of the plunger. Alternatively or in addition, the main body is adapted to be squeezed against the barrel by the user during use of the syringe.

In yet another type of embodiment, the clip is securable onto a head of the plunger, and the progress slowing means includes at least one clamp securable to the barrel creating dynamic friction with the barrel as the plunger is pushed into the barrel. The clamp may be made resilient and be adapted to grip the barrel when secured thereto. Alternatively or in addition, the main body may be adapted to be squeezed against the barrel by the user during use.

In another embodiment, the progress slowing means includes a spring element mechanically coupled between the plunger and the barrel. When the user exerts a force on the plunger to push the plunger into the barrel, the spring element tends to resist the user's force by generating a spring force tending to push the plunger out of the barrel. In this embodiment, preferably, the clip is securable to the plunger head, and a second clip is provided securable to a finger grip flange of the syringe. The ends of the spring element are preferably attached to the clips.

The invention also includes a hand-held hypodermic syringe with integral dosage rate control. As with conventional syringes, the inventive syringe has a barrel and a plunger reciprocatably movable into and out of the barrel. The inventive syringe also includes means for selectively slowing a rate of progress of the plunger into the barrel.

In one embodiment, the progress slowing means includes a plurality of teeth formed on one of the barrel and the plunger and a mating tooth formed on the other of the barrel and the plunger. The mating tooth is abuttable against the plurality of teeth to creates a resistive force that retards the descent of the plunger into the barrel when the plunger is also pushed into the barrel. Preferably, the plunger is made resilient, so that when the user presses down on the plunger, the user also presses the plunger against the barrel so as to press the mating tooth against the teeth. The mating tooth may be disposed on an exterior surface of the barrel, in which case and the plurality of teeth may be formed on a distally extending flange integral with the plunger. Alternatively, the mating tooth may be disposed on an interior surface of the barrel.

The syringe may also include a brake formed on an exterior of the barrel and a hole formed in the barrel. The mating tooth is disposed on an end of a brake exterior surface of the barrel and extends into the hole to contact the plurality of teeth on the plunger. As an optional feature to this embodiment, a collar may be provided at least partially threadedly engaged with the barrel below the brake and extending at least partially parallel with the brake. When the collar is rotated so as to move the collar in a proximal direction, the collar reaches more proximally on the brake and squeezes the mating tooth into the hole with greater force.

Alternatively, the inventive syringe may include the thumb tip rest mentioned above. The thumb tip rest is formed at a proximal end of the barrel adapted to allow a user to place a tip of a thumb thereupon during dispensing of contents of the syringe. When the user applies force to a head of the plunger with the tip of the thumb pressing on the thumb tip rest, force is substantially applied about an axis through the upper thumb joint. The thumb tip rest may be a substantially vertical surface or a substantially horizontal surface as above. In the vertical-surfaced version the thumb tip is pressed against the vertical surface and the first joint of the thumb is rocked downward against the head of the plunger. As before, the vertical surface may be provided with a significantly higher coefficient of friction than the rest of the syringe, teeth adapted to accommodate the thumb tip of a user between adjacent of the teeth, or both. Preferably, the vertical surface is sufficiently close to the plunger so that at least the head of the plunger is laterally pressable against the vertical surface while the plunger is being pushed downward into the barrel. In such a mode of operation, the higher coefficient of friction (or the teeth, or both) creates a resistive force that retards the descent of the plunger into the barrel when the user presses the head of the plunger against the vertical surface while pushing the plunger downward into the barrel.

The inventive syringe may also include a plunger stop and/or finger grip indentations.

The device may be made in the form of a clip-on structure to be attached to existing conventional syringes, or in the alternative, a syringe may be constructed with the device integral thereto.

The invention provides a mechanical solution to a molecular problem, specifically, the tendency of a plastic syringe plunger to show erratic "stick-slip" behavior which results in an unpredictable rate of delivery of medication, including sudden surges. Stick slip behavior arises from the interaction of the elastomer used to manufacture the syringe piston, the lubricant and the syringe cylinder. In the embodiments employing a thumb tip rest, the thumb is made to act as a second class lever, where the fulcrum is at one end (the thumb tip), the force is applied at the other end (the first distal joint), and the load (the plunger head) is in between, close behind the fulcrum. Second class levers of this type inherently have a mechanical advantage of greater than 1, because the moment arm of the force is always greater than the moment arm of the load. As such, it is easier to overcome the plunger's static friction, and the speed at which the plunger is moved is reduced. Leverage is improved, the thumb's range of motion per injected volume is much larger, and control becomes much finer and more easily applied.

The invention can be used to superimpose strong and sharply defined stopping forces along the direction of travel of the syringe plunger, using friction braking, direct opposition, or clicker action to provide positive control of the plunger movement. The objective is to achieve a slow, incremental manual injection stroke without requiring complicated or expensive stepper motors or similar mechanical devices.

It is not completely necessary to manufacture new components to achieve the invention. The inventive syringe brake can be incorporated into the manufacture of a syringe by slightly modifying the shapes of the moldings for the existing syringe cylinder and plunger. Thus, in some embodiments, the advantages can be achieved with no additional parts or assembly steps, and no added manufacturing cost. Low manufacturing cost is essential for a disposable syringe.

For smaller injections, i.e., less than 10 units or so from a 50-unit syringe, the use of the horizontal thumb tip is adequate. For larger injections, the vertical thumb tip rest is preferred. Since the height of the vertical rest can be freely set or extended, it can be readily adjusted to accommodate the desired injection volume, up to the full capacity of the syringe. Large injections are performed stepwise, in 10-unit segments for example. At the end of each 10-unit segment, the thumbtip is re-positioned to a new pivot point, lower along the vertical track, and a new injection segment is then initiated.

BRIEF DESCRIPTION OF THE DRAWINGS

FIGS. 14A-C are perspective drawings of a seventh embodiment of a syringe delivery rate control device in accordance with the invention.

DETAILED DESCRIPTION OF THE PREFERRED EMBODIMENTS

Description will now be given of the invention with reference to the attached FIGS. 1-16. It should be understood that these drawings are exemplary in nature and in no way serve to limit the scope of the invention, which is defined by the claims appearing hereinbelow.

Figure 1A:
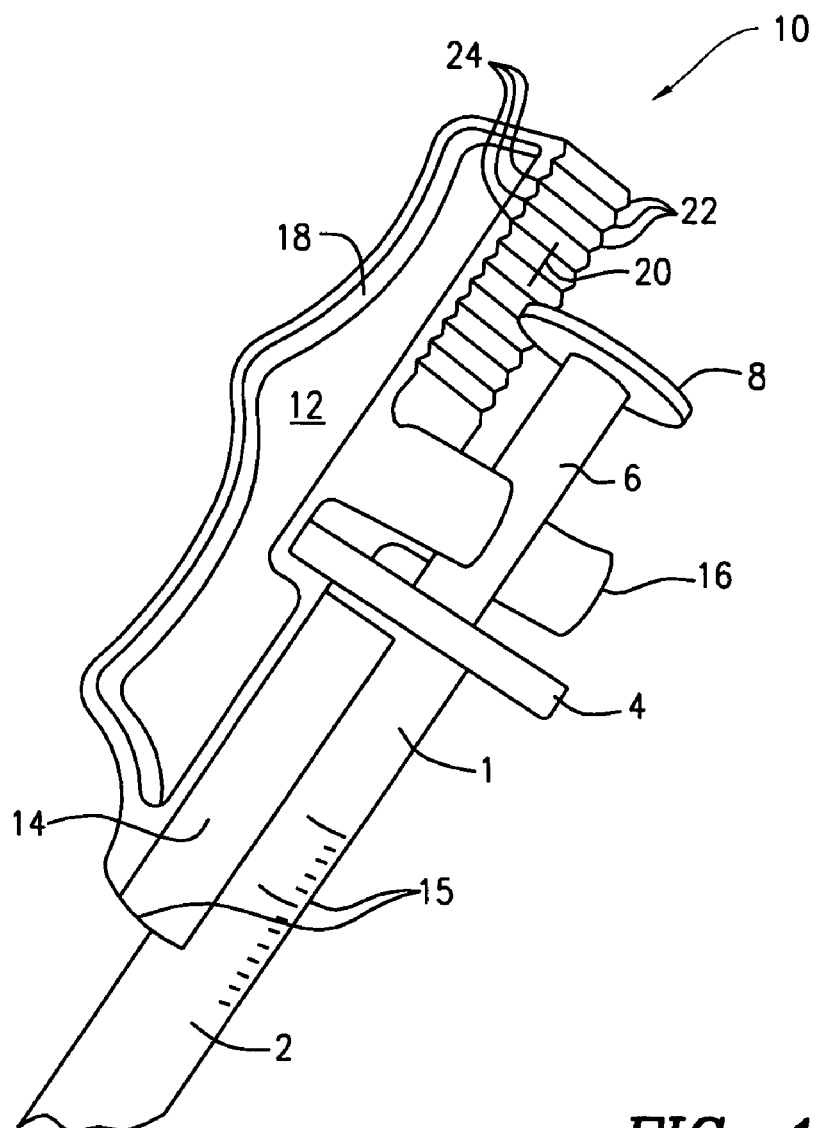
FIG. 1A is a perspective drawing showing a preferred embodiment of a syringe delivery rate control device in accordance with the invention.

A preferred embodiment of the invention is shown in FIG. 1 in relation to a typical manual hypodermic syringe 1 (shown in outline). The conventional syringe 1 has a barrel 2, finger grips 4, and a plunger 6 having a plunger head 8. Conventionally, the user grasps the syringe about barrel 2 between his index and middle fingers just below finger grips 4. The user then places his thumb atop plunger head 8. When the user squeezes his thumb and first two fingers together, the two fingers press under finger grips 4 and the thumb pushes plunger 6 downward into barrel 2, thereby dispensing the contents of the syringe. As described above, this process is adversely affected by the "stick-slip" effect at slow injection speeds, and a large bolus of medicine is delivered all at once. It would be more desirable to administer medicines at a slow, even rate. Device 10 of FIGS. 1-5 enables the user to accomplish this objective through increased leverage, oppositional braking, or both.

The inventive device 10 is attachable to an existing syringe 1 in the manner shown in FIG. 1. Device 10 has a main body 12 which may be formed as a single piece of plastic or similar material. Body 12 includes a clip 14 which has at least one (but preferably a pair of) resilient arms 15. Arms 15 have a curved interior hollow specifically adapted for receiving the exterior of barrel 2 of syringe 1. Different sized clips 14 may be created to accommodate different sized barrels 2, however if a single size of clip 14 is manufactured, it is likely that it can be made sufficiently resilient to accommodate most standard sizes of barrels. As shown in FIG. 1, barrel 2 is inserted into clip 14 so that finger grips 4 are above clip 14. Plunger stop 16 also extends from main body 12 above clip 14. The primary function of plunger stop 16 is to prevent plunger 6 from entering barrel 2 beyond a specific point. Thus, when the plunger is being depressed (to be described below), plunger head 8 will at some point abut against plunger stop 16 and will prevent plunger 6 from further downward travel into barrel 2.

Disposed on the opposite side of main body 12 from clip 14 are finger grips 18 which allow the user to grasp the device more comfortably and securely during use.

Figure 1B:
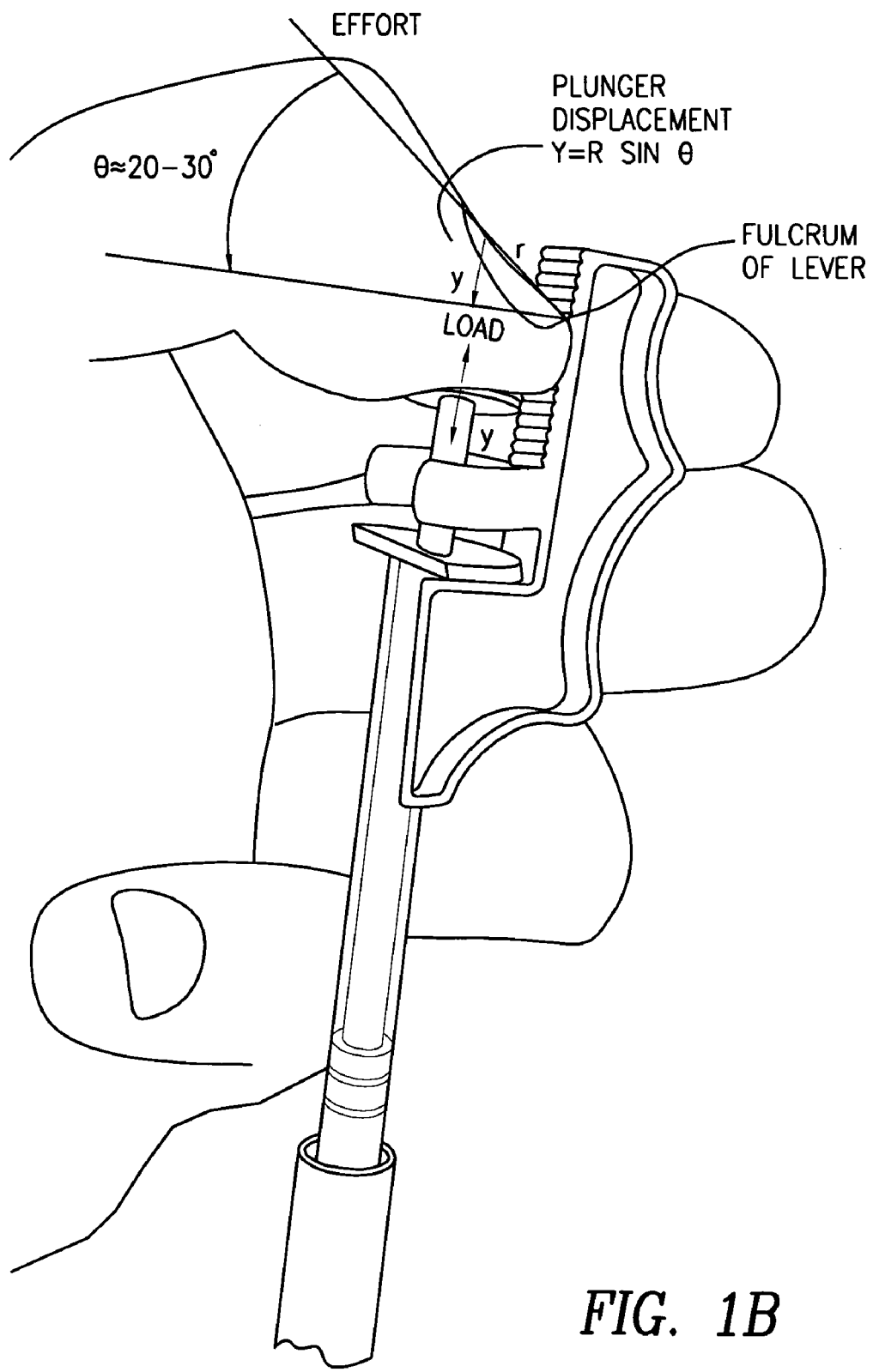
FIG. 1B is a perspective drawing of the embodiment of FIG. 1A in a force diagram.

Every embodiment of the invention includes some mechanism for gaining better control of (and thus slowing) rate of progress of the plunger into the barrel. This is conceptually accomplished in one of at least two ways. First, as shown in FIG. 1B, the mechanical advantage of the thumb is greatly increased by shifting the fulcrum of the thumb from the third distal joint to the thumb tip, thereby making the moment arm of the load (the distance from the plunger head to the thumb tip) much shorter than the moment arm of the effort (from the tip to the first distal joint) and shortening the distance the load travels (letter y in FIG. 1B). In other words, the invention enables the user to use his thumb as a second class lever instead of a third class lever as with conventional injection techniques.

In addition or in the alternative, the dynamic frictional resistance of the plunger may be increased to make it closer to (or equal to or greater than) the static frictional resistance of the plunger (i.e., the friction caused by continuing to move the plunger will be increased with respect to the static friction needed to be overcome just to begin to move the plunger).

Figure 2:
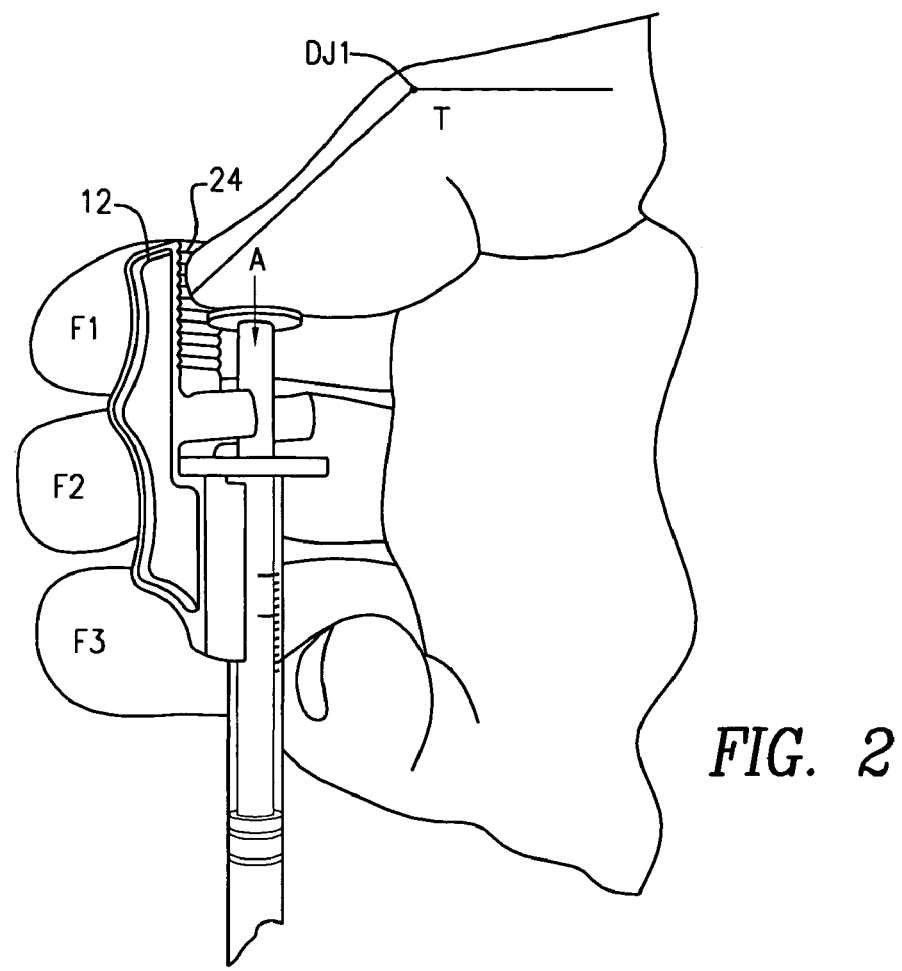
FIG. 2 is a schematic illustrating the use of the syringe delivery rate control device of FIG. 1 with a user's thumb in a first position.
Figure 3:
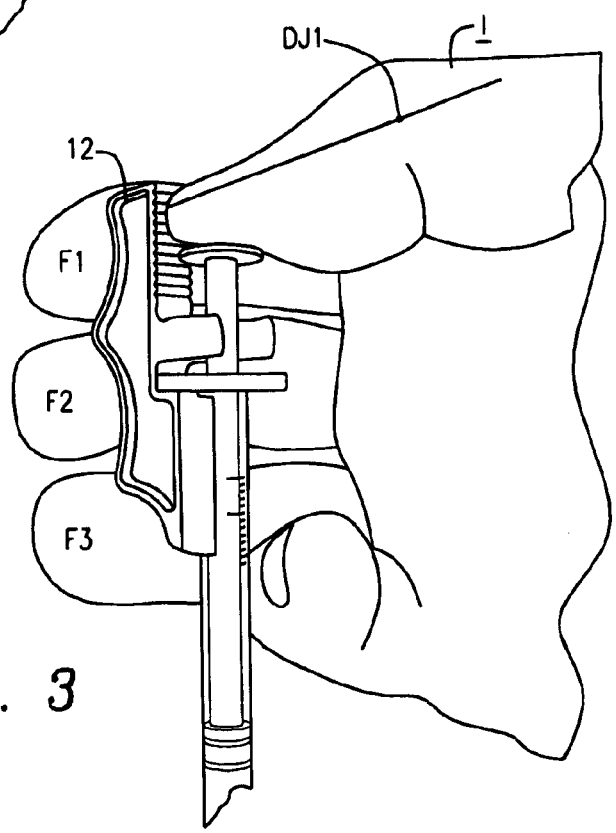
FIG. 3 is a schematic illustrating the use of the syringe delivery rate control device of FIG. 1 with a user's thumb in a second position.

In the preferred embodiment, shown in FIGS. 1-5, main body 12 includes a vertical surface 20 which may be used to slow the rate of progress of the plunger in either of the two ways listed above. As shown in FIG. 1, vertical surface 20 is preferably provided with teeth 22, between adjacent of which are troughs 24. In addition or in the alternative, vertical surface 20 may be provided with a "no-skid" coating or layer which has a significantly higher coefficient of friction than the rest of main body 12. In the preferred mode of operation, as shown in FIGS. 2-5, the user presses the tip of his thumb against vertical surface 20, more preferably in a trough 24. The first distal joint DJ1 of the thumb T is preferably angled as shown in FIG. 2. The ball of the thumb is positioned atop plunger head 8. The user's first, second, and/or third fingers F1-F3 are preferably positioned in finger grips 18. When it is desired to dispense the contents of the syringe, the user pivots the most distal phalange about the first distal joint DJ1 of the thumb T only while maintaining contact against vertical surface 20. The result is that the proximal end of the first distal joint (i.e., substantially at the first knuckle) moves downward, pressing against the plunger head. The end of this motion is shown in FIG. 3 as arrow A. Note that this downward rolling motion is produced by the extension of the first phalange of the thumb, as opposed to the flexing of the entire thumb used conventionally to empty a syringe.

Since the moment arm of the force being generated (from DJ1 to thumb tip) is now much greater than the moment arm of the load being moved (from thumb tip to plunger head), there is greater mechanical advantage of the thumb and much less plunger movement and speed as compared to conventional syringe usage, thereby allowing the user to move the plunger in a much finer fashion and have far greater control over its movement.

Figure 4:
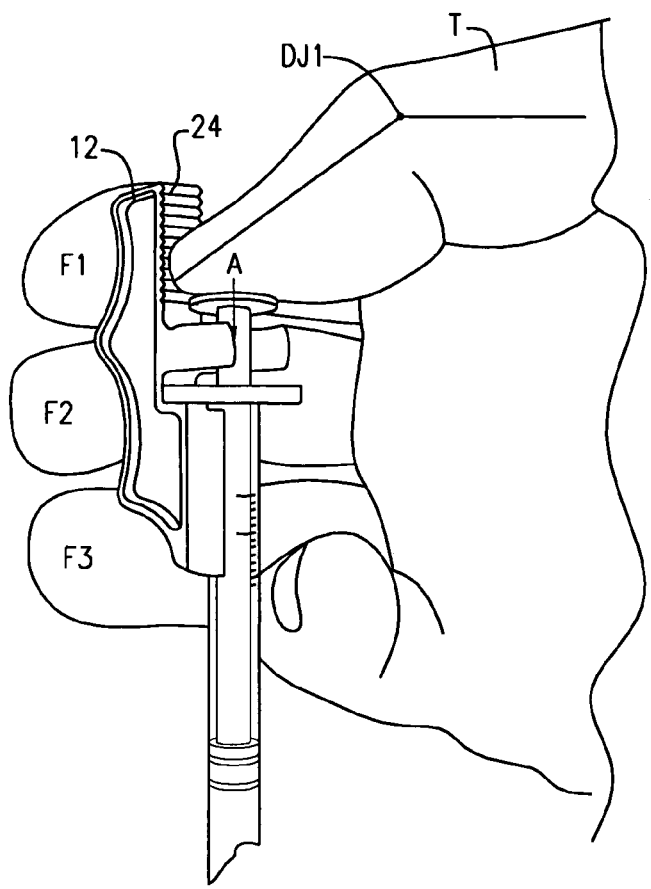
FIG. 4 is a schematic illustrating the use of the syringe delivery rate control device of FIG. 1 with a user's thumb in a third position.
Figure 5:
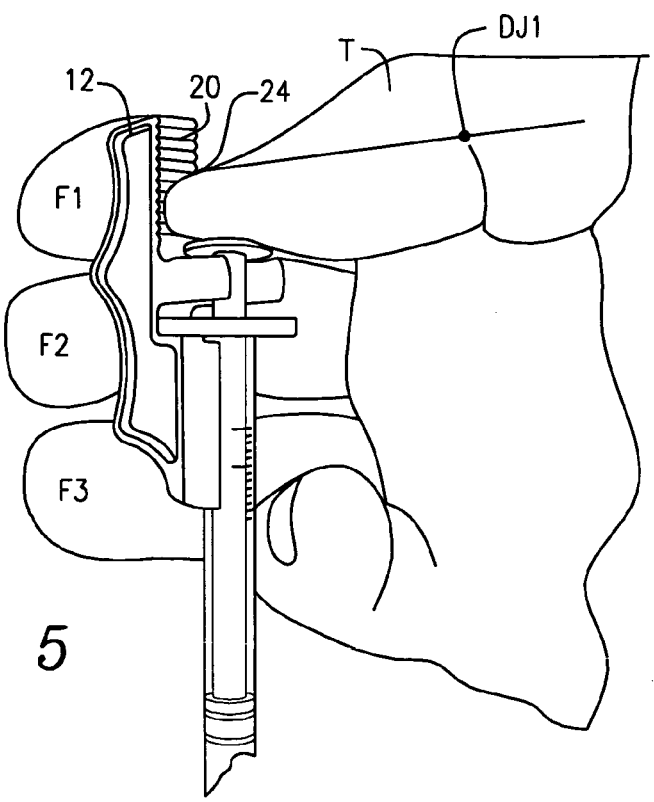
FIG. 5 is a schematic illustrating the use of the syringe delivery rate control device of FIG. 1 with a user's thumb in a fourth position.

The thumb tip may be re-placed at a different location on vertical surface 20 (e.g., where the plunger stopped at the end of the first "roll"), as shown in FIG. 4, and the above-described "rolling" motion of the first joint of the thumb would be repeated to dispense additional medicine. The end of the second roll is shown in FIG. 5. The process is repeated until the desired amount of medicine is dispensed or until plunger 8 abuts against plunger stop 16 (see FIG. 1).

The embodiment of FIGS. 1-5 may also be used in the other manner of the invention, i.e., to increase the dynamic frictional resistance of the plunger to make it closer to (or equal to or greater than) the static frictional resistance of the plunger. It may be tempting for the user to simply press plunger head 8 against vertical surface 20 in the direction of arrow B of FIG. 1 while pressing downward on plunger head 8 at the same time. Whether vertical surface 20 is provided with a "no-skid" high friction layer or teeth 22 (or both), dragging the side of plunger head 8 against vertical surface 20 while pushing it downward into the barrel greatly increases the resistive force of the plunger.

Opposition to the motion of the plunger slows and limits the runaway motion of the plunger induced by the stick slip effect. As a result, the motion of the plunger may be finely controlled. One advantage of this method of using the device is that, when teeth are provided, the plunger head will "click" as it passes over each tooth, providing an audible and tactile signal to the user. Each tooth brings the plunger to a decisive halt, and may be used as a way of metering out, in pulses, very small aliquots of medicine. The plunger may be stopped after passing over a predeterminable number of teeth. Dosage markings may be made on teeth 22 or on main body 12 near troughs 24 so that the dosage may be precisely loaded, monitored and delivered.

As shown in FIG. 1, injection retarder 10 is preferably a clip-on device attachable to a conventional plastic syringe. Injection retarder 10 is preferably made as a single piece of plastic, however other materials are contemplated. It is preferred that at least clip 14 be made from a resilient material (such as plastic) so that it may be snapped onto the barrel and stay put. Rack 20 may, in other embodiments, include any non-skid surface, that is, a surface offering an increased coefficient of friction. Several effective no-skid surfaces may be created from carborumdum paper, polyisoprene with molded-in teeth, smooth polyisoprene, or a rubberized, knurled, or otherwise roughened surface of essentially any material The non-skid surface can be molded or machined into the device, or attached to it. The toothed surface is superior, because of its predictable and reliable escapement action in arresting the syringe plunger 6 after each incremental injection of medication.

Figure 6:
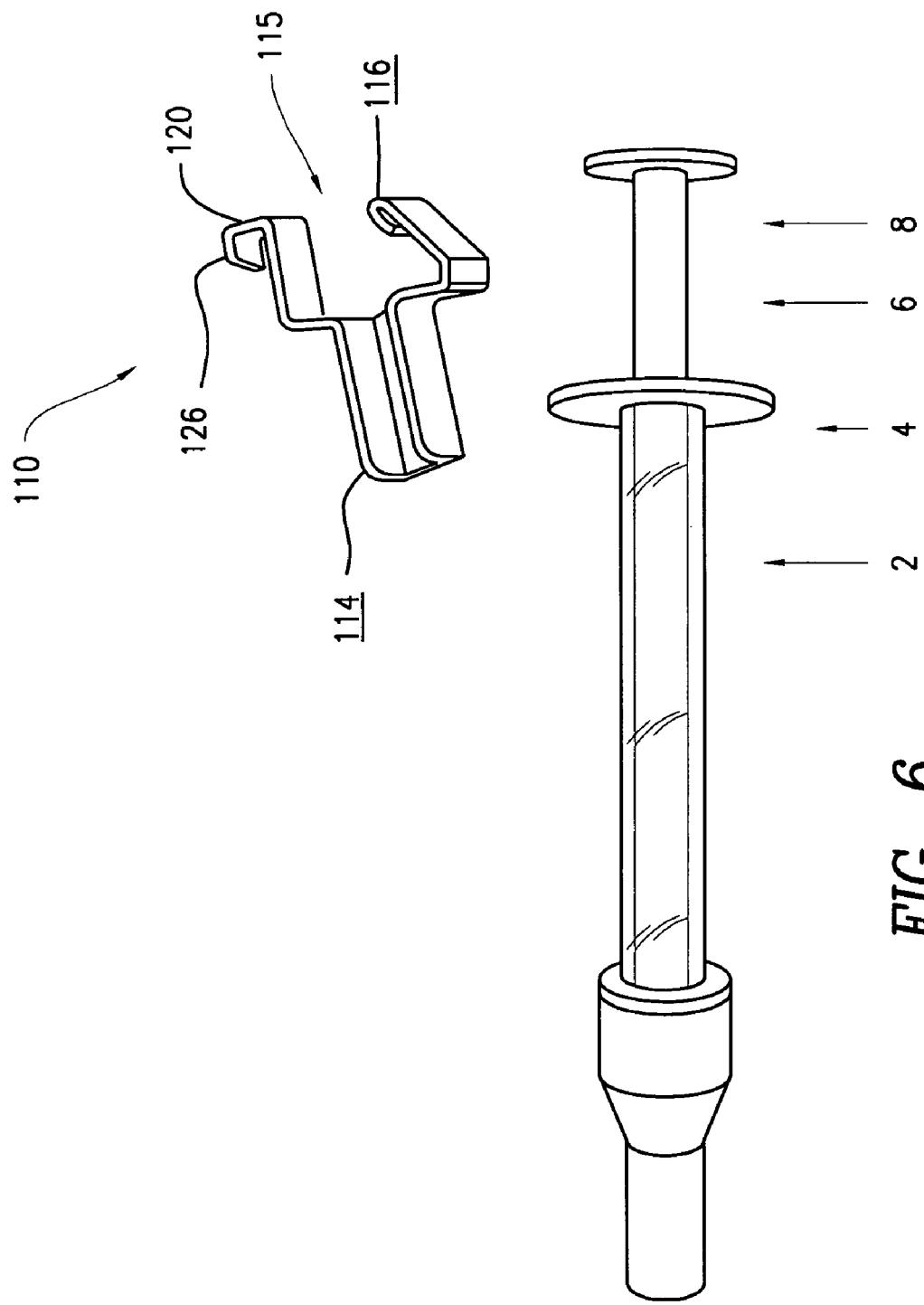
FIG. 6 is a perspective drawing showing a second embodiment of a syringe delivery rate control device in accordance with the invention next to a conventional syringe.
Figure 7:
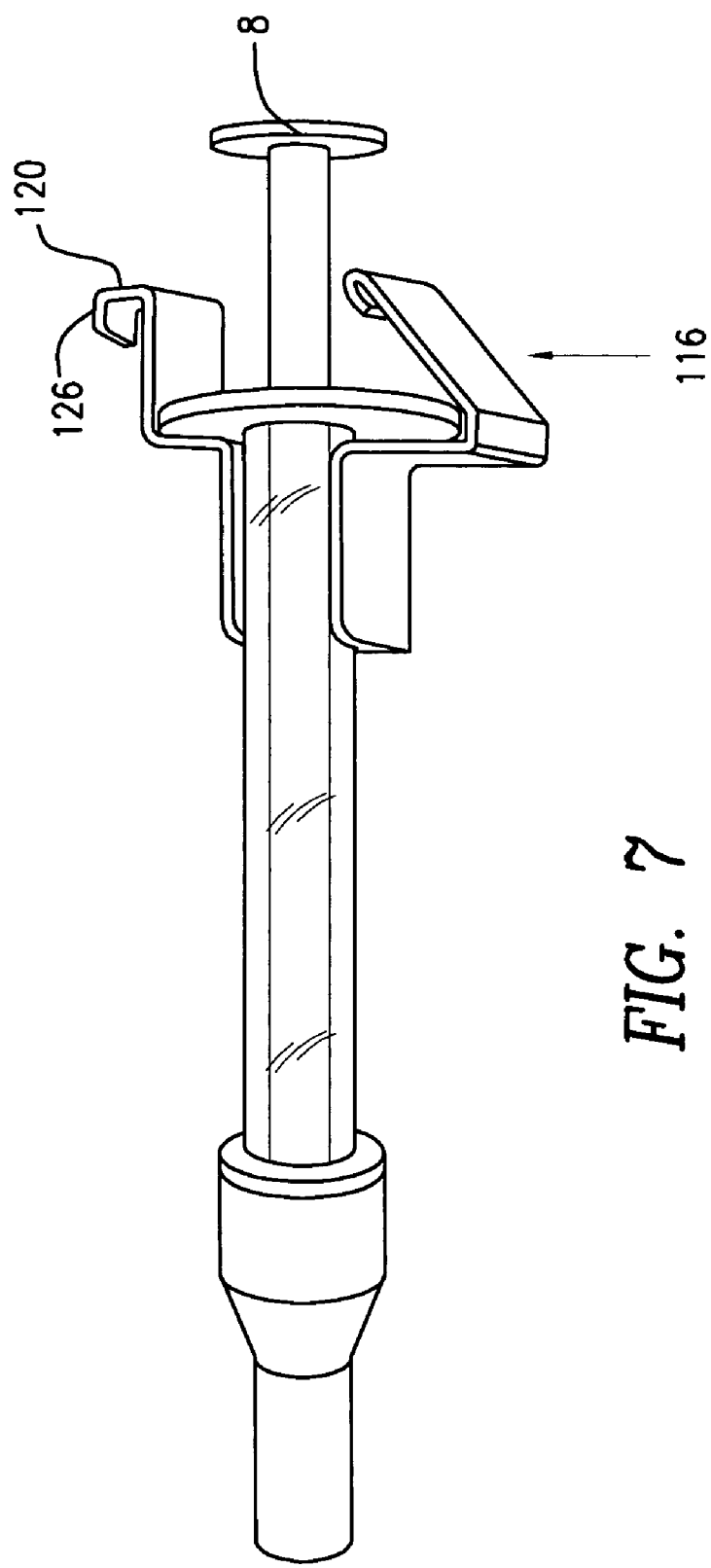
FIG. 7 is a perspective drawing showing the embodiment of the inventive syringe delivery rate control device of FIG. 6 secured to a conventional syringe.
Figure 8:
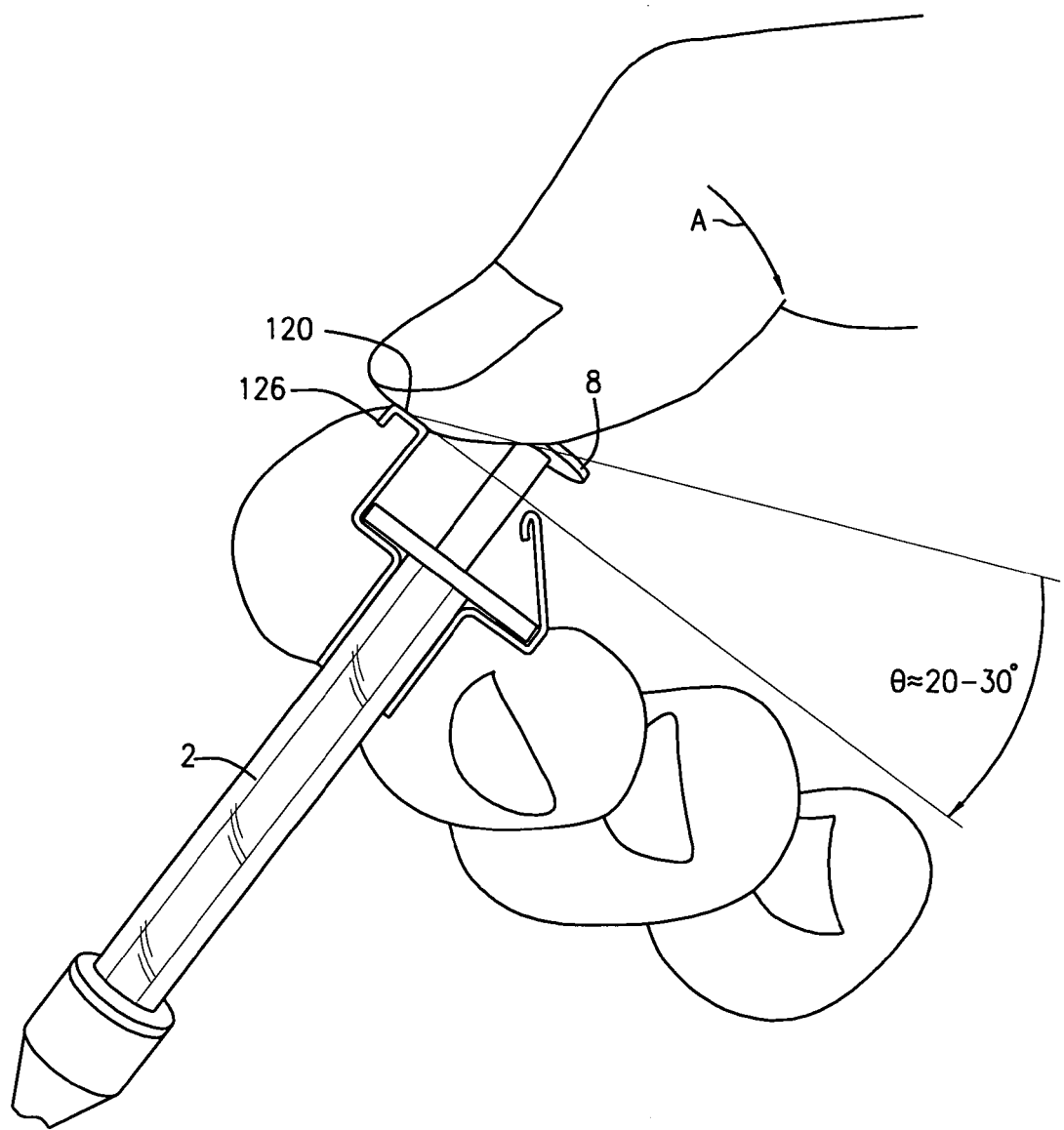
FIG. 8 is an elevational drawing showing the embodiment of the inventive syringe delivery rate control device of FIG. 6 being used.
Figure 9:
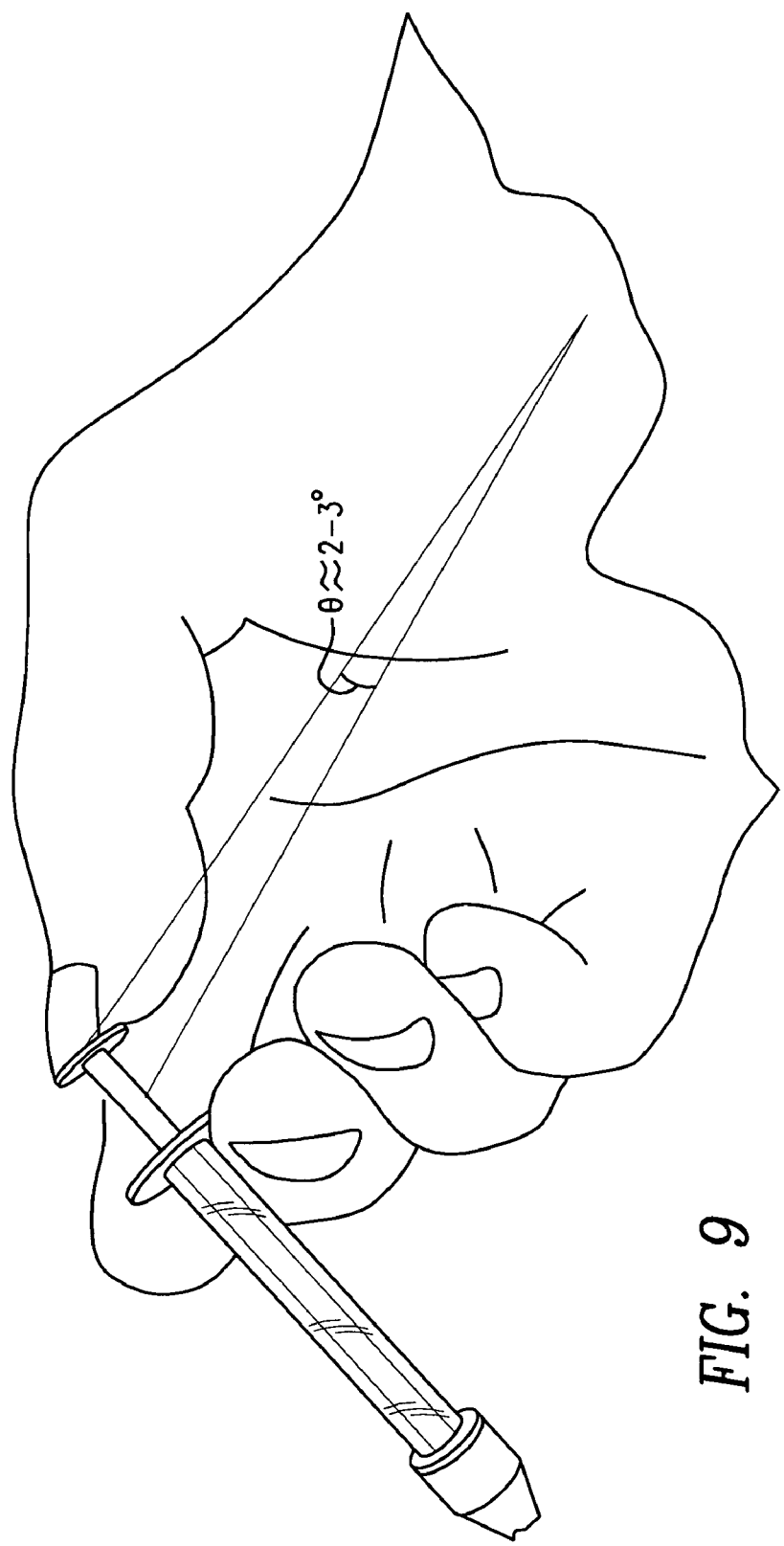
FIG. 9 is an elevational drawing showing a conventional syringe being used in a conventional manner.

FIGS. 6-8 depict an alternate embodiment of the inventive injection retarder 10. This embodiment offers only enhanced leverage; no braking is available. In FIGS. 6-8, injection retarder 110 is configured slightly differently than brake 10. Clip 114 is securable around barrel 2 of a syringe, and injection retarder 110 is provided with channel 115 into which syringe finger grip flanges 4 are disposable. As before, a plunger stop 116 is provided to delimit the range of motion of plunger 6 into barrel 2. The chief difference between injection retarder 10 and injection retarder 110 concerns the surface upon which the user rests or presses his thumb. In brake 10, the surface is vertical surface 20. In injection retarder 110, the relevant surface is horizontal surface 120. As shown in FIG. 8, the user places the tip of his thumb atop horizontal surface 126 and angles his first distal thumb joint upwards. The ball of the user's thumb is placed on plunger head 8. The user then pivots his thumb joint downward in the direction of arrow A as shown in FIG. 8 (it is substantially the same movement as shown in FIGS. 2-5). The angular movement of the first distal joint during this movement is approximately 25-30°. By contrast, if the user were to inject himself (or another) via the conventional method shown in FIG. 9 without the invention, the entire thumb becomes the lever arm for the force around where the thumb connects to the wrist, and the angular movement is only about 2-3°. Thus, as mentioned above, by moving the fulcrum, much finer control of the movement of the plunger is realized. The end 126 of horizontal surface 120 is curled downward to avoid a sharp edge and minimize the risk of a cut or abrasion.

The embodiment of FIGS. 6-8 is preferably made as a single piece and can be made from either sheet or stamped metal or molded plastic. In this embodiment, clip 114 is preferably resilient so that it may be snapped onto the barrel and stay put.

In using both devices 10 and 110, the first distal joint of the thumb swings downward from a pivot point which is positioned, by the invention, in front of the syringe body. Thus, the pivot point used in dispensing medicine is now moved vastly forward by using the invention of the above embodiments. On a conventional syringe, the thumb pivots from a joint at the wrist. In devices 10 and 110, the thumb pivots from a point on surface 20 (or 120), a point just ahead of the syringe body. One purpose of moving the fulcrum to a point ahead of the syringe body is to increase the arc swept by the first knuckle of the thumb as it depresses the plunger of the syringe. This makes it much easier to slowly dispense medication from the syringe. The class of the lever represented by the thumb is also changed by shifting the fulcrum to the thumbtip. Using a conventional syringe in the conventional manner is using the thumb as a third class lever, analogous to a mousetrap. A third class lever is configured for speed, and thus has a mechanical advantage of less than 1. In contrast, use of the inventive device on a syringe enables the thumb to act as a second class lever, e.g., like a garlic press or nut cracker. A second class lever has excellent mechanical advantage and moves the load (i.e. the plunger) slowly.

The basic functioning of the above embodiments is depicted in FIG. 1B and is representable by the following equation:

$$y = r \sin \theta \quad (1)$$

where y is displacement r is the radius and θ is the angle.

As long as distance between the pivot point and point at which power is applied to the plunger is kept very short (meaning, the radius, r, is kept short) it does not matter from where on the thumb one chooses to pivot. If r is small, the displacement, y, will be kept small, and the plunger will move slowly.

There exist four possible pivot points for the thumb—the tip, the first knuckle (from the nail), the second knuckle, and the socket point at the wrist. A point selected near any of these joints, or pivots, could theoretically be used the drive the syringe plunger. There are four fundamental reasons to use the invention and choose the thumb tip: opposition, dosage, visibility, and repeatability.

Opposition. Opposition or bracing for the thumb is essential because of the stick-slip effect. Opposition helps the thumb quickly stop itself. It keeps the "slip" from turning into a runaway slide, delivering a 2-unit or larger bolus. In the above embodiments of FIGS. 1-8, surfaces 20 and 120 provide serve both as a pivot and a flat surface secured to the syringe against which to brace the thumb. When the user overcomes the stiction, the thumb does not translate this release into a surge of medication, thanks to the solid opposition of the mechanical stop against which the thumb tip is constantly pushing.

Dosage and pivot shifting. The thumb tip is free, while the three other possible pivots are inhibited in their mobility, especially the wrist socket. The thumb tip can be placed in any convenient location. This is important because for a large dose, it is necessary to change pivot points in the course of the injection, as shown in FIGS. 2-5. Freehand methods might work adequately for small doses, which can be accomplished at one squeeze, but not for doses of greater than about 8 units from a 50-unit syringe. This is because to accommodate a large dose (25 units, say) you need to be able to move the pivot point. This is easy to do with a thumb tip fulcrum and a vertical surface (e.g., surface 20). The user simply moves the thumb tip down the runway to establish a fresh pivot point, from time to time, as the injection plunger progresses downward. By contrast, it is not easy to use the first or second knuckle as the chosen pivot by, perhaps, shifting the syringe in one's hand in order to follow a long plunger stroke to its conclusion. It is very undesirable to manipulate the syringe much after the needle has been planted in tissue.

Visibility. Devices 10 and 110 can be clipped onto the syringe in such a way that the graduation marks on the syringe barrel can be easily read and the progress of the injection can be easily monitored. This is difficult if the syringe is gripped deep inside the user's hand, as it would have to be if one were to position the plunger at one of the other possible pivot points.

Precision and repeatability. The inventive surface for the thumb tip pivot is precisely positionable, using manufacturing techniques such as molding or machining, so that the radius, r, is kept very small. As a result the injection procedure as performed with the invention is reliably slow and repeatable.

In terms of slowing down the plunger, and thus the rate of injection, the performance of device 10 with the vertical surface 20 is superior to that of device 110. This is because the vertical surface can be positioned very close to the plunger, minimizing the radius, r, and thus the displacement, y. The thumbnail inserted between the teeth of device 10 provides an excellent pivot and an anchor against runaway injection. In addition, with device 10 the force of the thumb is directed forward, rather than downward in the direction of travel of the plunger. This also helps prevent uncontrolled surges. Instead, the plunger moves downward in a succession of tiny budges, and these budges effectively demark the increments of injected volume. One can decisively halt the injection after any such incremental volume, or pulse, has been delivered to the tissues. This is important because one way to judge the success of the invention is to ask how little medication can be injected before the plunger can be brought to a halt. Recall that in a conventional injection from a 50-unit insulin syringe, the smallest volume that can be fairly repeatably delivered to the tissues was a slug of about 2.5 to 3.0 units.

Experimentally, using a 50-unit capacity syringe, it has been determined that device 10 can be used to inject medication in incremented pulses as small as 0.3 units, while device 110 has been able to inject a succession of incremented pulses as small as 0.5 units. In either case, this is a very substantial improvement on the 2.5-unit surges delivered in an uncontrolled manner when the same syringe is used conventionally.

Figure 10C:
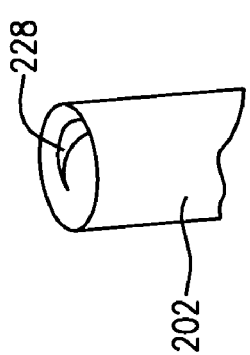
FIGS. 10A-C are perspective drawings of two versions of a third embodiment of a syringe delivery rate control device in accordance with the invention.
Figure 10B:
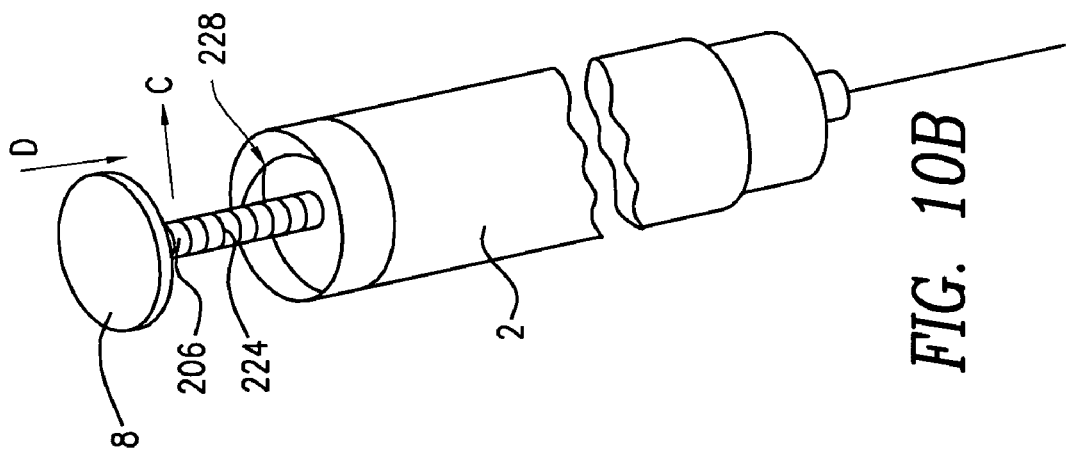
Figure 10A:
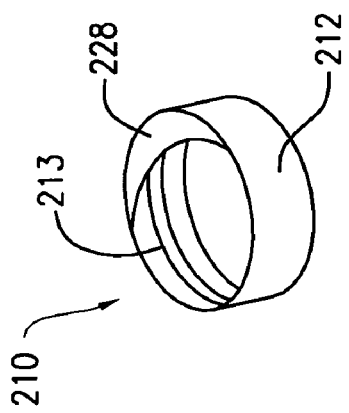

Many other forms of the inventive syringe brake are contemplated. For example, FIGS. 10A-C depict injection retarder 210 having a short, substantially cylindrical main body 212 that is securable onto the proximal end of barrel 2 (se FIG. 10B). The interior of main body 212 may be provided with ribs 213 for creating a friction fit with the end of the barrel; alternatively, threads could be provided for screwing injection retarder 210 onto a customized barrel having mating threads (not shown). An engaging pawl or tooth 228 is formed on main body 212 projecting inward towards the center where the plunger would be disposed. As shown in FIG. 10B, brake 210 is preferably used with a customized plunger 206 having teeth (or knurling) 224. In operation, plunger 206 is pressed sideways against tooth 228 in the direction of arrow C while it is depressed into barrel 2 in the direction of arrow D. The increased frictional resistance caused by teeth 224 dragging over tooth 228 slows the progress of the plunger. The transition from tooth to tooth arrests the "slip" of the plunger, limiting and defining the volume that can be delivered with each incremental downward move of the plunger. The spacing of the teeth can be set to correspond to some useful increment of injection volume, e.g., 0.3 or 0.5 units. This movement also produces a clicking sound and tactile feedback, which can aid the user in metering out dosages of medicine. FIG. 10C shows an alternative embodiment in which tooth 228 is formed integrally with barrel 202. All of the same principles enumerated above with the previous embodiment apply to the FIG. 10C embodiment.

Figure 11A:
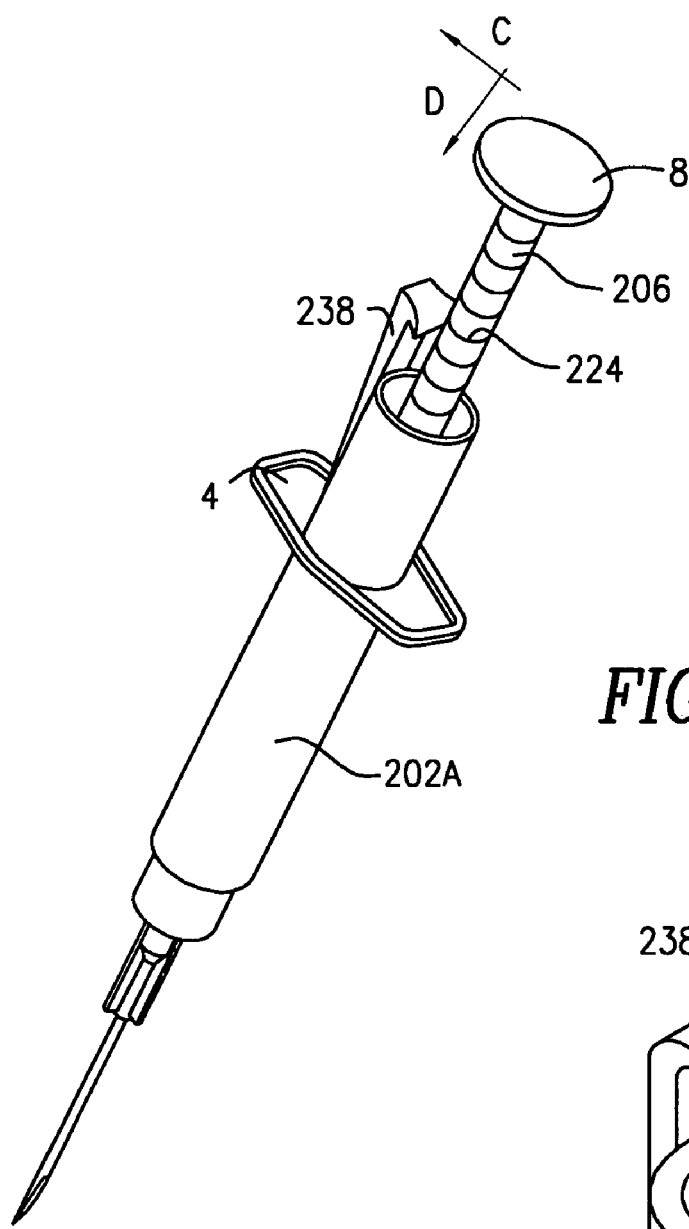
FIGS. 11A-B are perspective drawings of two versions of a fourth embodiment of a syringe delivery rate control device in accordance with the invention.
Figure 11B:
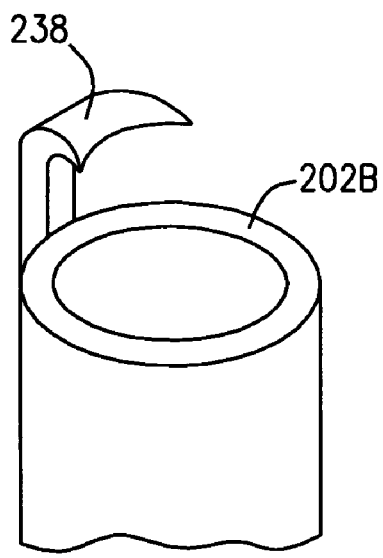

FIGS. 11A-B depict another clicker-style braking embodiment formed integrally with the syringe. Plunger 206 includes teeth 224, however the barrel includes a curved brake 238 which extends past the proximal end of the barrel. Again, plunger 206 is pressed against brake 238 in the direction of arrow C while being depressed into the barrel in the direction of arrow D. In FIG. 11A, brake 238 extends from the side of barrel 202A at its proximal end, e.g., from near the finger grip flanges 4. In FIG. 11B, brake 238 extends directly out of the top of barrel 202B. Brake 238 may be made of resilient plastic or metal to be biased towards plunger 206.

Figure 12A:
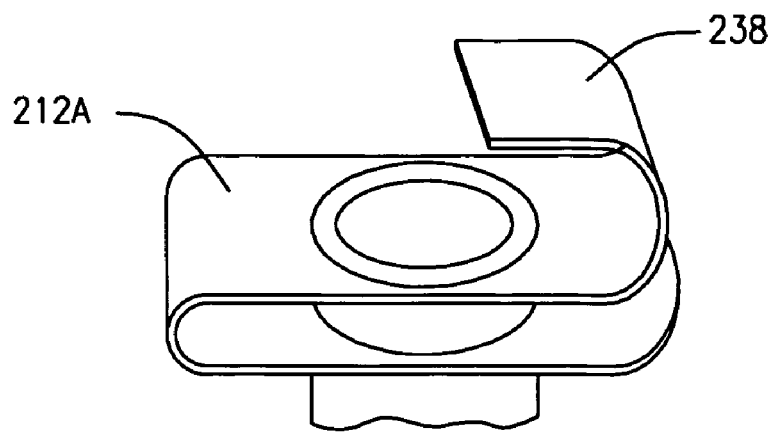
FIGS. 12A-B are perspective drawings of a fifth embodiment of a syringe delivery rate control device in accordance with the invention.
Figure 12B:
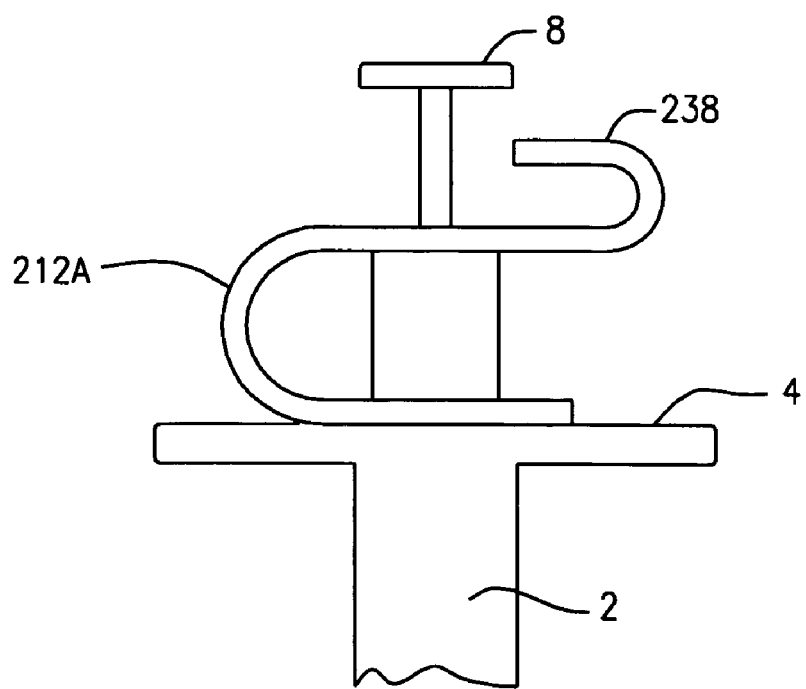

FIGS. 12A-B depict a clip-on version of the FIG. 11 embodiment. Main body 212A is somewhat S-shaped in cross section and, as shown in FIG. 12B, is disposable on top of finger grip flanges 4. This embodiment may be made from plastic or sheet or stamped metal.

Figure 13A:
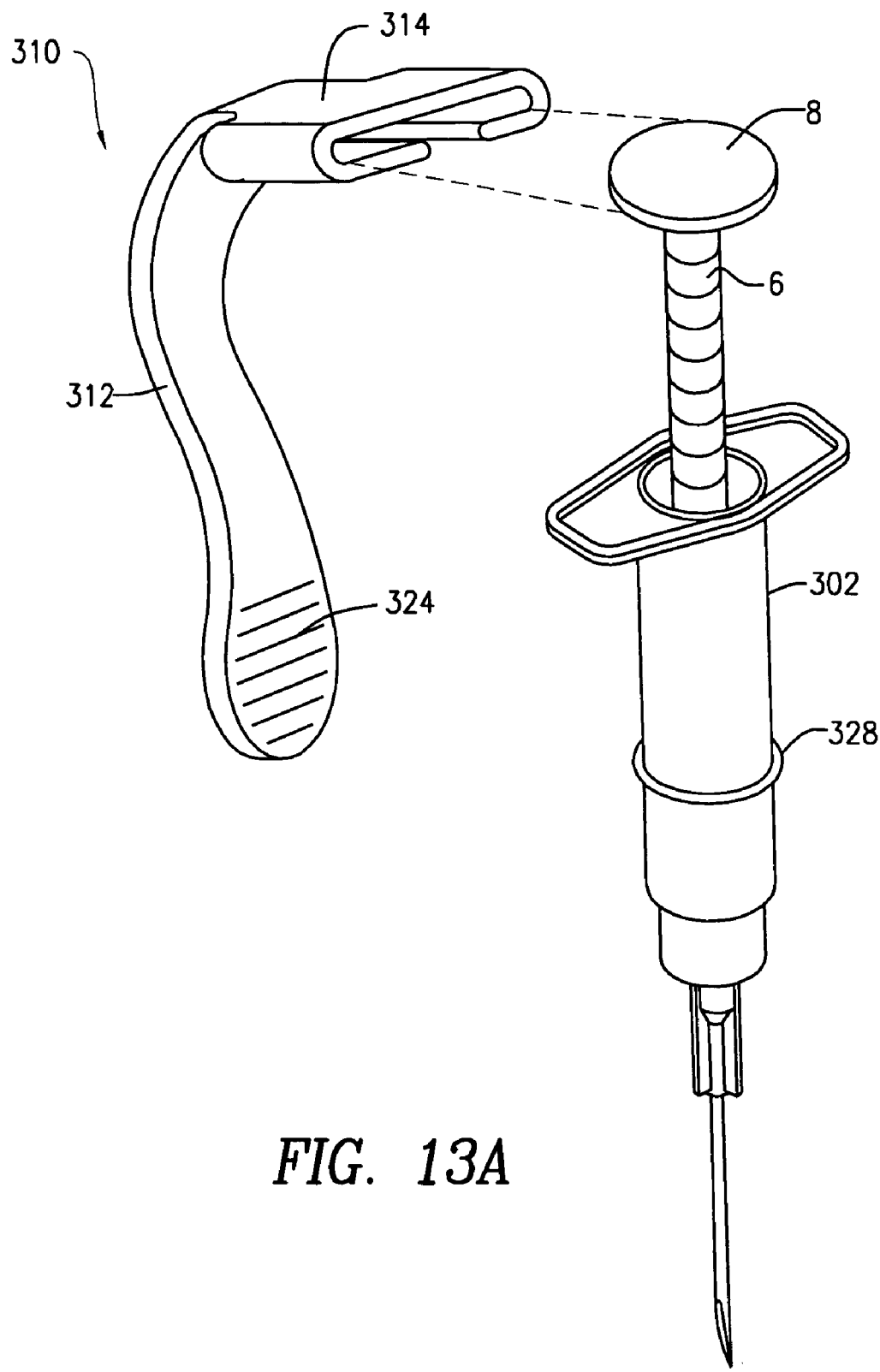
FIGS. 13A-B are perspective drawings of a sixth embodiment of a syringe delivery rate control device in accordance with the invention.
Figure 13B:
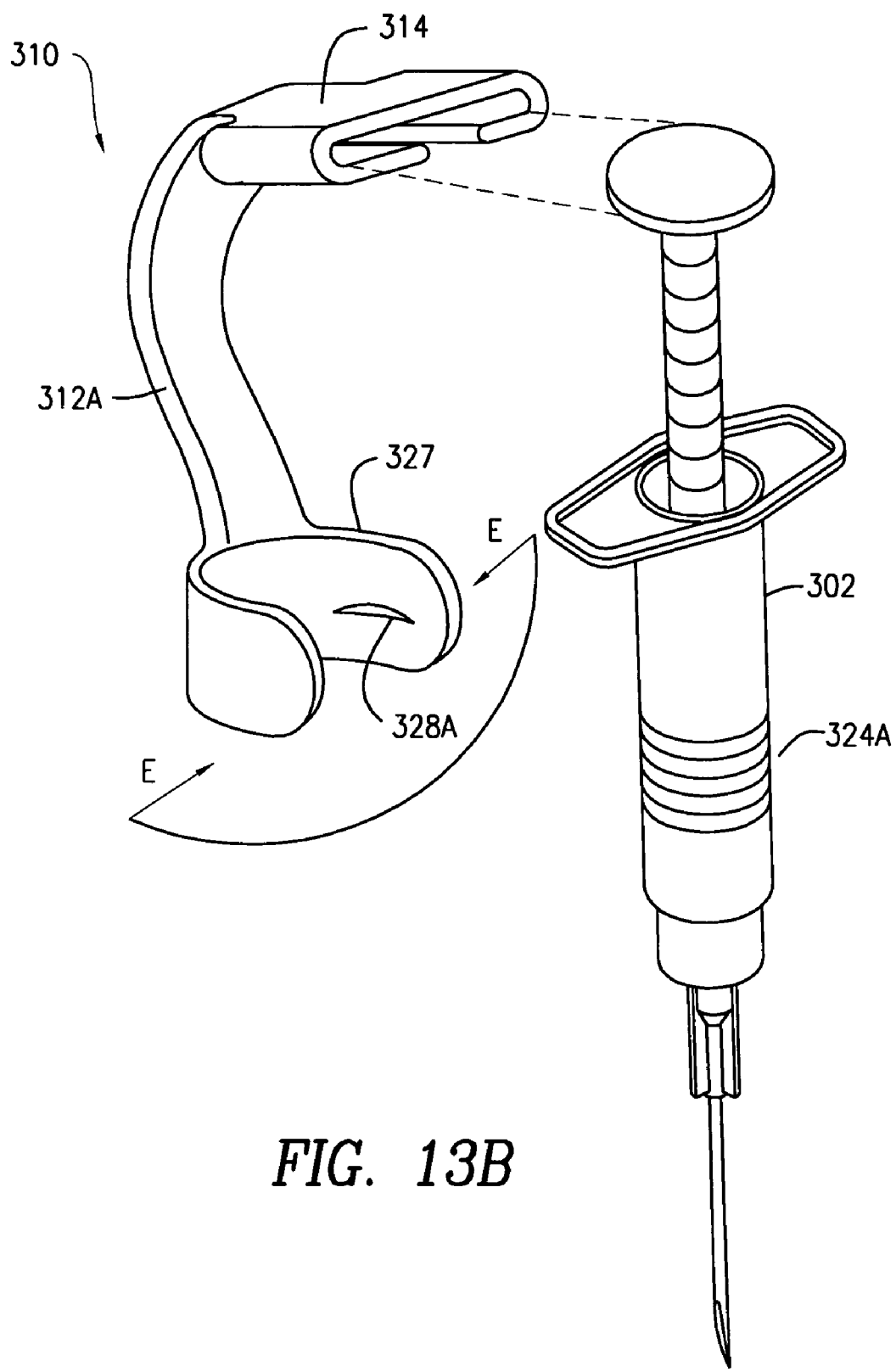
Figure 14A:
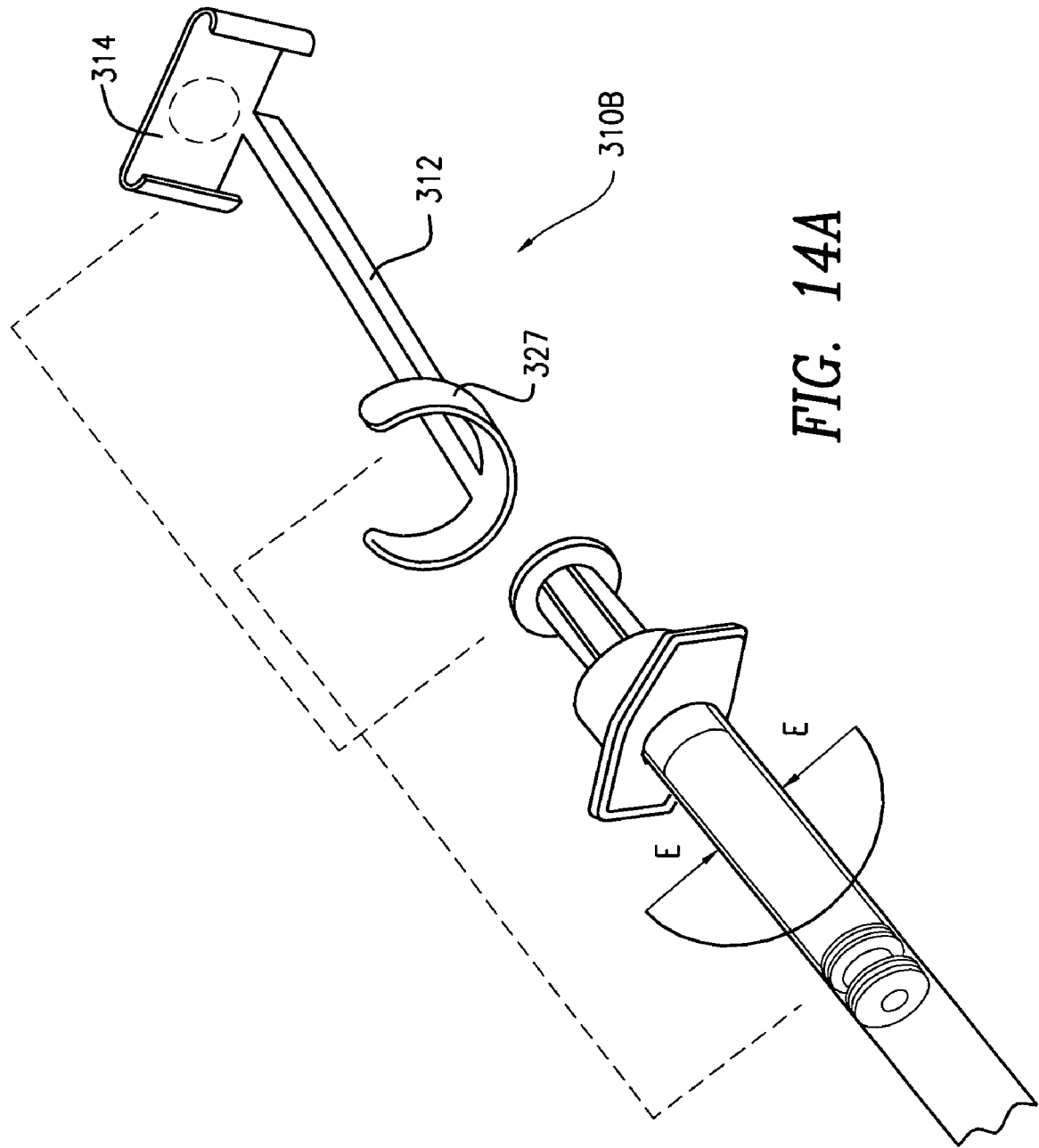

Injection retarder 310 is depicted in FIG. 13. In FIG. 13A, clip 314 is formed at one end of main body 312 and is adapted to be secured onto plunger head 8. At the other end of main body 312 are formed teeth or knurling 324 which are adapted to engage an annular brake or tooth 328 formed on barrel 302. Main body 312 may be curved and made from a resilient material so that when clip 314 is secured onto plunger head 8, teeth 324 are naturally pressed against annular tooth 328. A similar embodiment, injection retarder 310A, is shown in FIG. 13B. Here, main body 312A includes a distal barrel gripper 327 which fits around the barrel of a plunger. In the embodiment shown in FIG. 13B, tooth 328A engages teeth or knurling 324A formed on barrel 302A. Barrel gripper 327 may be made from a resilient material and dimensioned to fit snugly on the barrel to insure the engagement of tooth 328A and teeth 324A. In the alternative or in addition, the user may squeeze barrel gripper 327 in the direction of arrows E to increase such engagement and therefore the frictional resistance thereof. FIG. 14 depicts a simpler embodiment 310B which may be secured to and work on conventional syringes. Here, barrel gripper 327 may be resilient and/or squeezed as before to increase the sliding friction between it and barrel 2. FIGS. 14B and C depict two of the many different shapes this embodiment may take.

There are two ways to use a device of the type shown in FIG. 14. One is to squeeze the clip against the body of the syringe barrel to create, and vary, dynamic friction braking to control and retard the descent of the plunger. The other method is to place opposed fingers on the barrel, so that one or more fingers lie directly in the path of the clip, and let the clip "bulldoze" the fingers. The fingers, by opposing the progress of the clip, can provide direct muscular opposition to the downward force of the thumb on the plunger.

In all of the embodiments for clicker action described above, the toothed surface may be replaced with a high coefficient of friction surface. This can be accomplished by shaping (as by knurling) or by layering with a higher friction material (e.g., polyisoprene), or both.

Figure 15:
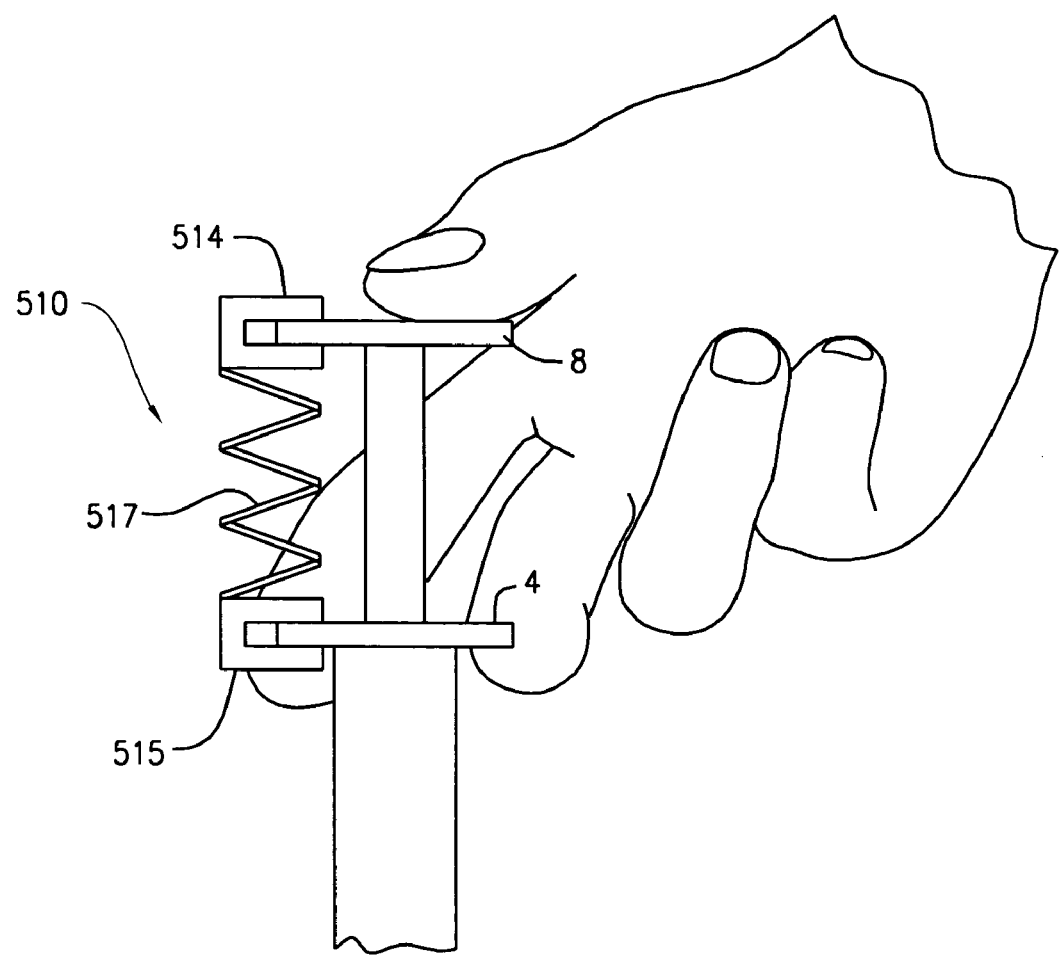
FIG. 15 is a side elevational drawing of an eighth embodiment of a syringe delivery rate control device in accordance with the invention.

FIG. 15 depicts another embodiment of the inventive plunger progress slowing mechanism. Here, brake 510 includes a spring element 517 mechanically connected between the plunger and barrel of a syringe. In the drawing, one end of spring element 517 is attached to a clip 514 which is securable to plunger head 8, while the other end is attached to clip 515 which is securable to finger grip flange 4. As the plunger is depressed, the spring element generates a resistive force in the opposite direction, tending to resist the progress of the plunger into the barrel. Other connective structure may be employed.

Figure 16A:
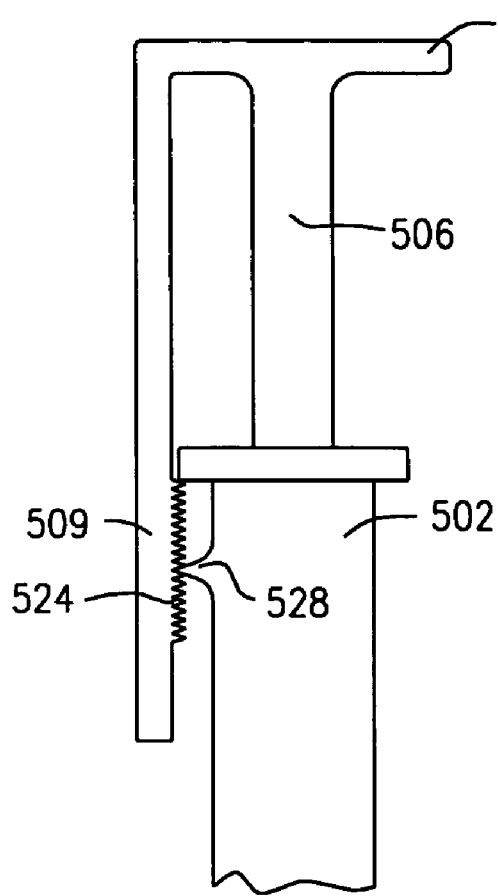
FIGS. 16A-D are elevational and partial sectional drawings of a ninth embodiment of a syringe delivery rate control device in accordance with the invention.
Figure 16B:
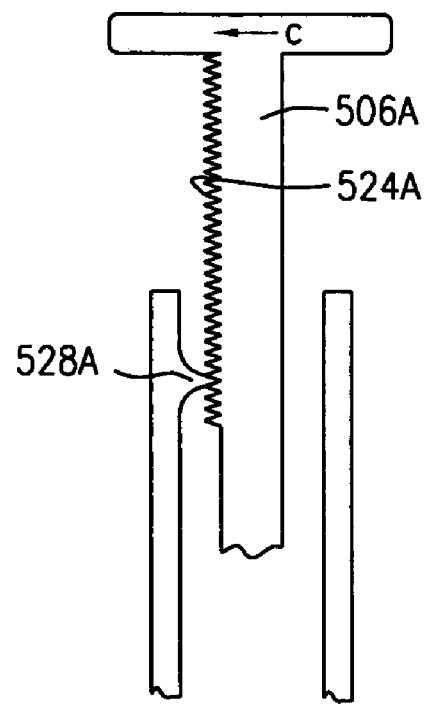
Figure 16C:
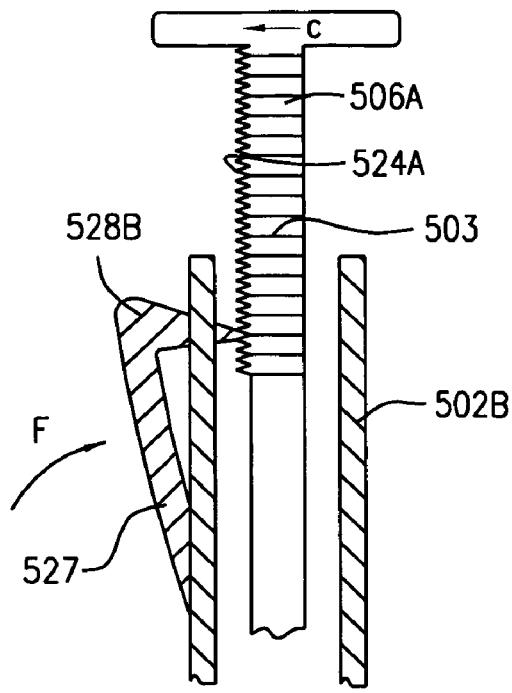
Figure 16D:
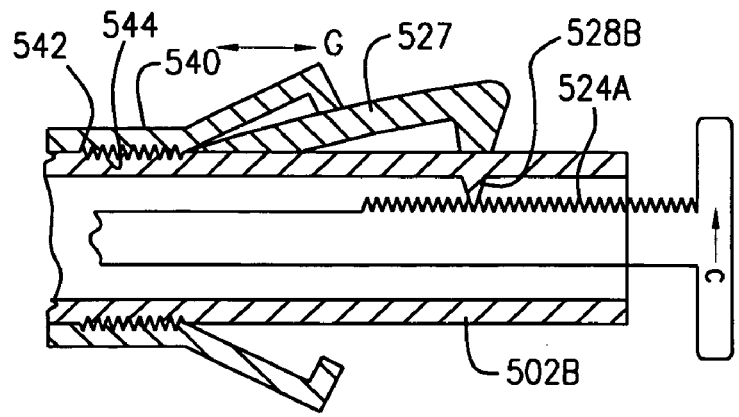
Figure 2:
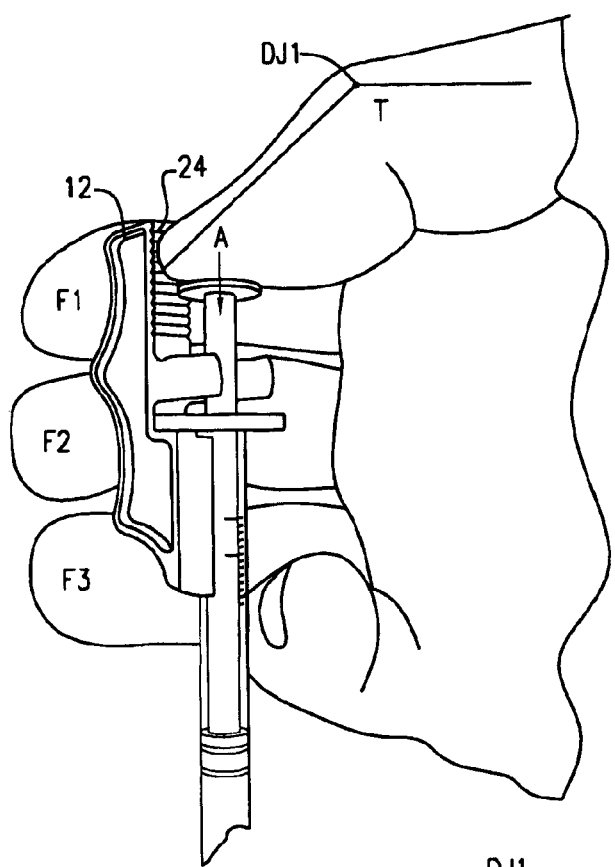

FIGS. 16A-D depict a variety of modified syringes that have plunger progress slowing mechanisms built integrally therein. FIG. 16A depicts a syringe having a modified plunger 506 having plunger head 508 with a downwardly extending flange 509. The distal end of flange 509 is provided with teeth or knurling 524; barrel 502 is provided with a mating tooth or pawl 528 on its exterior. Flange 509 may be made from a resilient material so that it is biased against tooth 528. Alternatively or in addition, the user may squeeze flange 509 against tooth 528 during use. FIG. 16B illustrates a similar embodiment having teeth 524A formed on plunger 506A, and tooth 528A formed on the interior of barrel 528A. FIG. 16C shows another embodiment having brake 527 integrally formed with barrel 502B. Tooth 528B protrudes through a hole in barrel 502B to engage teeth 524A on plunger 506A. Indicia 503 may be printed on plunger 506A to assist in dosage metering. FIG. 16D adds a collar 540 which can adjust the amount of pressure brake 527 places on teeth 524A. Collar 540 includes threads 542 which engage mating threads 544 on the exterior of barrel 502B. When collar 540 is rotated, is moves along arrow G; the further in the proximal direction the collar is moved, the tighter it squeezes brake 527, and the greater the frictional force between the brake and the teeth will be generated.

The invention is not limited to the above description. For example, FIGS. 1-5 show a substantially vertical thumb tip support surface, and FIGS. 6-8 show a substantially horizontal thumb tip support surface. However, an angled support surface (i.e., an angle between 0°, or horizontal, and 90°, or vertical) may be employed without departing from the scope of the invention. In addition, one may apply both leverage and braking action to the relative motion of the syringe barrel 2 and the plunger 6. This can be accomplished by judiciously combining on a single syringe more than one of the embodiments discussed above. For example, one can combine the leverage—only device of FIG. 6 with the clicker device of FIG. 16C or D.

Further, any descriptions of manufacturing processes are not meant to be limiting but merely exemplary and demonstrative. Also, while some embodiments are shown as a clip-on device attachable to a conventional syringe and others are shown as integral to a modified syringe, it should be understood that any of the clip-on structures may be integrated into a modified syringe, and any of the modified syringe structures may be utilized in a clip-on device.

Having described various embodiments of the invention, it should be understood that the invention is not limited to the above description or what is shown in the drawings. Rather, the invention is defined by the scope of the claims appearing hereinbelow and their equivalents to those of ordinary skill in the art.

What is claimed is:

1. An injection retarder syringe attachment for manually controlling the delivery rate of a hand-held hypodermic syringe, comprising:

a main body having a proximal section and a distal section, said distal section having a clip substantially immovably securable onto a hypodermic syringe, said proximal section of said main body at least partially extending above the finger grips of the barrel adjacent to a plunger of the syringe, but extending on only one side of the plunger, when said clip is secured to the syringe; and a thumb tip rest including a surface formed on said proximal section of said main body outside of and above the syringe barrel and unobstructed by any other portion of said syringe attachment adapted to allow a user to place a tip of a thumb substantially orthogonally on said surface during dispensing of contents of the syringe, said thumb tip rest adapted to allow the user to selectively slow a rate of progress of the plunger into the barrel, wherein when the user applies force to the head of the plunger with the pad of the thumb while the tip of the thumb is pressing on said thumb tip rest, with said thumb tip rest remaining stationary with respect to the syringe so as to act as a fulcrum for the thumb, force is substantially applied about an axis through the upper thumb joint.

2. An injection retarder syringe attachment for manually controlling the delivery rate of a hand-held hypodermic syringe according to claim 1, wherein said thumb tip rest comprises a substantially vertical surface extending substantially parallel to a longitudinal axis of the syringe barrel, wherein when the user applies force to the head of the plunger with the tip of the thumb pressing on said thumb tip rest substantially orthogonally, the thumb tip is pressed against said vertical surface and the first joint of the thumb is rocked downward with the pad of the thumb pressing against the head of the plunger, and force is substantially applied about the axis through the upper thumb joint.

3. An injection retarder syringe attachment for manually controlling the delivery rate of a hand-held hypodermic syringe according to claim 2, wherein said vertical surface has a significantly higher coefficient of friction than the rest of said main body.

4. An injection retarder syringe attachment for manually controlling the delivery rate of a hand-held hypodermic syringe according to claim 3, wherein said vertical surface is sufficiently close to the plunger so that at least the head of the plunger is laterally pressable against said vertical surface while the plunger is being pushed downward into the barrel, wherein said higher coefficient of friction creates a resistive force that retards the descent of the plunger into the barrel when the user presses the head of the plunger against said vertical surface while pushing the plunger downward into the barrel.

5. An injection retarder syringe attachment for manually controlling the delivery rate of a hand-held hypodermic syringe according to claim 2, wherein said vertical surface further comprises teeth substantially perpendicular to the longitudinal axis of the barrel adapted to accommodate the thumb tip of a user between adjacent of said teeth.

6. An injection retarder syringe attachment for manually controlling the delivery rate of a hand-held hypodermic syringe according to claim 5, wherein said vertical surface is sufficiently close to the plunger so that at least the head of the plunger is laterally pushable against said teeth while the plunger is being pushed downward into the barrel, wherein said teeth create a resistive force that retards the descent of the plunger into the barrel when the user presses the head of the plunger against said teeth while pushing the plunger downward into the barrel.

7. An injection retarder syringe attachment for manually controlling the delivery rate of a hand-held hypodermic syringe according to claim 2, further comprising finger grip indentations formed in a side of said main body opposite said clip behind said vertical surface.

8. An injection retarder syringe attachment for manually controlling the delivery rate of a hand-held hypodermic syringe according to claim 1, further comprising a plunger stop secured to said main body and extending above the barrel and in the path of the head of the plunger,
   wherein when a user presses down on the plunger head, the plunger moves into the barrel until the plunger head abuts said plunger stop and substantially prevents the plunger from bottoming out inside the barrel.

9. An injection retarder syringe attachment for manually controlling the delivery rate of a hand-held hypodermic syringe according to claim 1, wherein said thumb tip rest comprises a substantially horizontal surface extending above and outward from the proximal end of the barrel and substantially perpendicular to a longitudinal axis of the syringe barrel,
   wherein the thumb tip is pressed against said horizontal surface and the first joint of the thumb is rocked downward with the pad of the thumb pressing against the head of the plunger.

10. An injection retarder syringe attachment for manually controlling the delivery rate of a hand-held hypodermic syringe according to claim 1, wherein said thumb tip rest comprises means for increasing a dynamic frictional force exerted by the plunger against the force exerted by the user in depressing the plunger.

11. A hand-held hypodermic syringe with integral manual dosage rate control, comprising:
    a barrel;
    a plunger reciprocatably movable into and out of said barrel; and
    a thumb tip rest substantially immovably formed at a proximal end of said barrel outside and above said barrel and including a surface outside and above said syringe barrel adjacent said plunger and unobstructed by any other portion of said syringe adapted to allow a user to place a tip of a thumb substantially orthogonally thereupon during dispensing of contents of said syringe, said thumb tip rest adapted to allow the user to selectively slow a rate of progress of said plunger into said barrel,
    wherein when the user applies force to a head of said plunger with the pad of the thumb while the tip of the thumb is pressing on said thumb tip rest, with said thumb tip rest remaining stationary with respect to said syringe so as to act as a fulcrum for the thumb, force is substantially applied about an axis through the upper thumb joint.

12. A hand-held hypodermic syringe with integral manual dosage rate control according to claim 11, wherein said thumb tip rest comprises a substantially vertical surface extending substantially parallel to a longitudinal axis of said syringe barrel,
    wherein the thumb tip is pressed against said vertical surface and the first joint of the thumb is rocked downward with the pad of the thumb pressing against said head of said plunger.

13. A hand-held hypodermic syringe with integral manual dosage rate control according to claim 12, wherein said vertical surface has a significantly higher coefficient of friction than the rest of said syringe.

14. A hand-held hypodermic syringe with integral manual dosage rate control according to claim 13, wherein said vertical surface is sufficiently close to said plunger so that at least said head of said plunger is laterally pressable against said vertical surface while said plunger is being pushed downward into said barrel,
    wherein said higher coefficient of friction creates a resistive force that retards the descent of said plunger into said barrel when the user presses said head of said plunger against said vertical surface while pushing said plunger downward into the barrel.

15. A hand-held hypodermic syringe with integral manual dosage rate control according to claim 12, wherein said vertical surface further comprises teeth substantially perpendicular to the longitudinal axis of the barrel adapted to accommodate the thumb tip of a user between adjacent of said teeth.

16. A hand-held hypodermic syringe with integral manual dosage rate control according to claim 15, wherein said vertical surface is sufficiently close to said plunger so that at least said head of said plunger is laterally pushable against said teeth while said plunger is being pushed downward into said barrel,
    wherein said teeth create a resistive force that retards the descent of said plunger into said barrel when the user presses said head of said plunger against said teeth while pushing said plunger downward into said barrel.

17. A hand-held hypodermic syringe with integral manual dosage rate control according to claim 13, further comprising finger grip indentations formed behind said vertical surface.

18. A hand-held hypodermic syringe with integral manual dosage rate control according to claim 11, further comprising a plunger stop formed on said barrel and extending above said barrel and in the path of said head of said plunger,
    wherein when a user presses down on said plunger head, said plunger moves into said barrel until said plunger head abuts said plunger stop and substantially prevents the plunger from bottoming out inside the barrel.

19. A hand-held hypodermic syringe with integral manual dosage rate control according to claim 11, wherein said thumb tip rest comprises a substantially horizontal surface extending above and outward from the proximal end of the barrel and substantially perpendicular to a longitudinal axis of the syringe barrel,
    wherein the thumb tip is pressed against said horizontal surface and the first joint of the thumb is rocked downward with the pad of the thumb pressing against the head of the plunger.

* * * * *

UNITED STATES PATENT AND TRADEMARK OFFICE
CERTIFICATE OF CORRECTION

PATENT NO.        : 7,611,495 B1                                        Page 1 of 2
APPLICATION NO.   : 11/245827
DATED             : November 3, 2009
INVENTOR(S)       : Michael Gianturco It is certified that error appears in the above-identified patent and that said Letters Patent is hereby corrected as shown below:

In the drawings:

Delete Drawing Sheet 4 and replace with attached sheet.

In the claims:

col. 16, line 36, change "13" with --12-- therefor.

Signed and Sealed this

First Day of June, 2010

David J. Kappos
*Director of the United States Patent and Trademark Office*